United States Patent
Jones et al.

(10) Patent No.: US 7,273,927 B2
(45) Date of Patent: Sep. 25, 2007

(54) MDM2 SPLICE VARIANTS

(75) Inventors: Stephen N. Jones, Shrewsbury, MA (US); Heather Steinman, North Grafton, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 10/980,519

(22) Filed: Nov. 3, 2004

(65) Prior Publication Data

US 2005/0176075 A1    Aug. 11, 2005

Related U.S. Application Data

(60) Provisional application No. 60/517,318, filed on Nov. 3, 2003.

(51) Int. Cl.
*C07H 21/02* (2006.01)
*C07H 21/04* (2006.01)

(52) U.S. Cl. .................................... 536/23.1

(58) Field of Classification Search ................. None
See application file for complete search history.

(56) References Cited

U.S. PATENT DOCUMENTS 5,912,143 A * 6/1999 Bandman et al. ......... 435/69.1

OTHER PUBLICATIONS

Bowie et al (Science, 1990, 257:1306-1310).*
Burgess et al (J of Cell Bio. 111:2129-2138, 1990).*
Lazar et al (Molecular and Cellular Biology, 1988, 8:1247-1252).*
Chen et al. (1996, Mol. and Cell. Biol. 16(5):2445-2452).*
GenBank Accession No. NM 002392 (as downloaded Jun. 5, 2006).*
Boehringer Mannheim Biochemicals, 1994 Catalog, p. 93.*

* cited by examiner

*Primary Examiner*—Shanon Foley
*Assistant Examiner*—Catherine Joyce
(74) *Attorney, Agent, or Firm*—Fish & Richardson P.C.

(57) ABSTRACT

The invention provides polypeptide and polynucleotide splice variants of the mouse Mdm2 gene, including Mdm2-b, which is homologous to the human Hdm2-b variant, as well as host cells, vectors and transgenic mice comprising the variants, and methods for the use thereof.

7 Claims, 5 Drawing Sheets

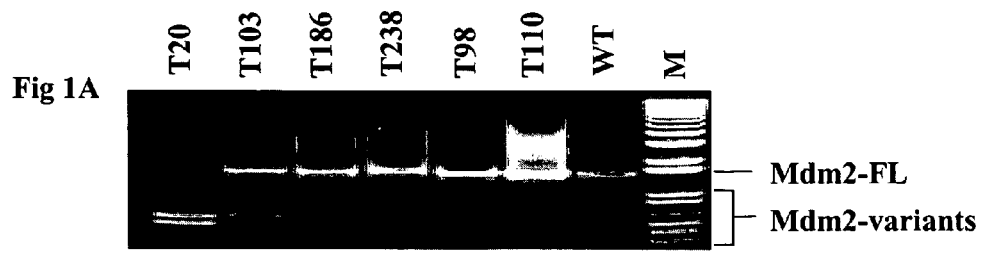

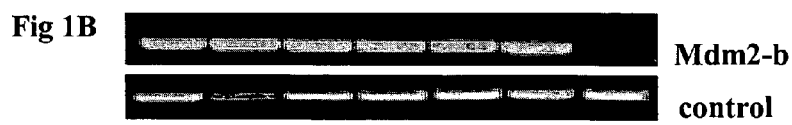

```
Fig 1C
1    MCNTNMSVPTDGAVTTSQIPASEQETLDYWKCTSCNEMNPPLPSHCNRCWALRENWLPED 60
     MCNTNMSV T+GA +TSQIPASEQETLDYWKCTSCNEMNPPLPSHC RCW LRENWLP+D
1    MCNTNMSVSTEGAASTSQIPASEQETLDYWKCTSCNEMNPPLPSHCKRCWTLRENWLPDD 60

61   KGKDKGEISEKAKLENSTQAEEGFDVPDCKKTIVNDSRESCVEE-NDDKITQASQSQESE 119
     KGKDK EISEKAKLENS QAEEG DVPD KK    ND++E C  EE +++K Q   SQES+
61   KGKDKVEISEKAKLENSAQAEEGLDVPDGKKLTENDAKEPCAEEDSEEKAEQTPLSQESD 120

120  DYSQPSTSSSIIYSSQEDVKEFEREETQDKEESVESSLPLNAIEPCVICQGRPKNGCIVH 179
     DYSQPSTSSSI+YSSQE VKE  +EETQDK+ESVESS LNAIEPCVICQGRPKNGCIVH
121  DYSQPSTSSSIVYSSQESVKEL-KEETQDKDESVESSFSLNAIEPCVICQGRPKNGCIVH 179

180  GKTGHLMACFTCAKKLKKRNKPCPVCRQPIQMIVLTYF 217    SEQ ID NO:14 – Hdm2-b
     GKTGHLM+CFTCAKKLKKRNKPCPVCRQPIQMIVL+YF
180  GKTGHLMSCFTCAKKLKKRNKPCPVCRQPIQMIVLSYF 217    SEQ ID NO:12 – Mdm2-b
```

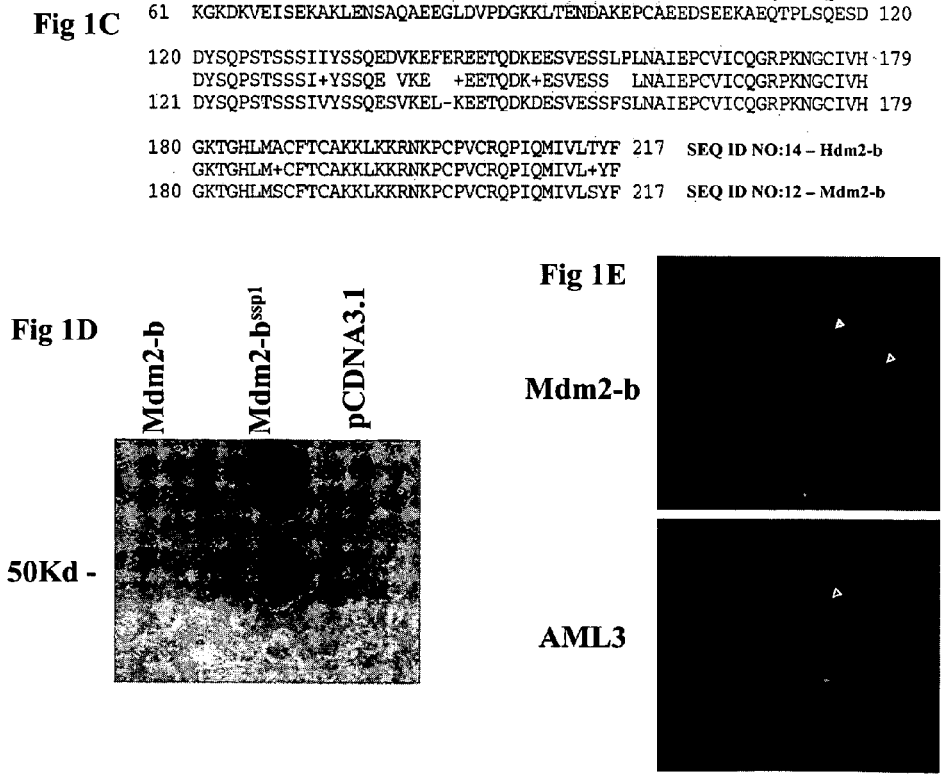

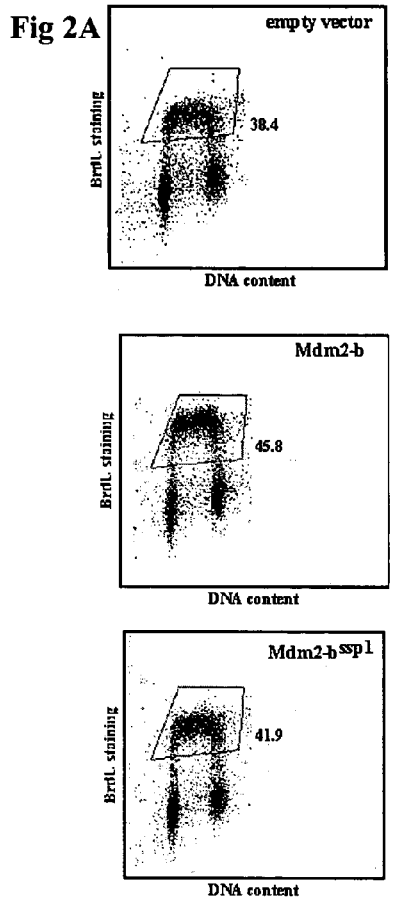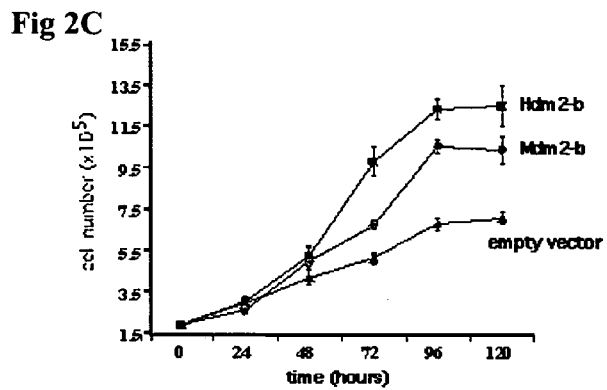

NIH3T3-pBabe    NIH3T3-Mdm2-b    NIH3T3-Mdm2-b$^{ssp1}$

Fig 4A
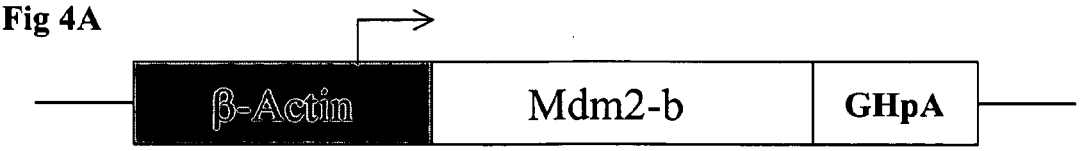
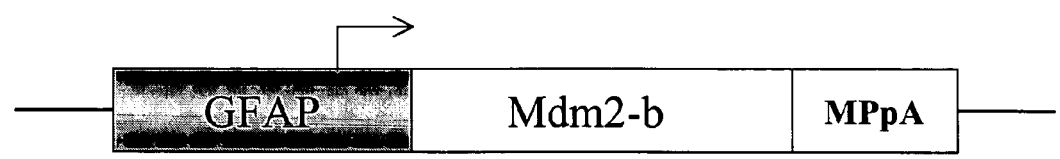
Fig 4B
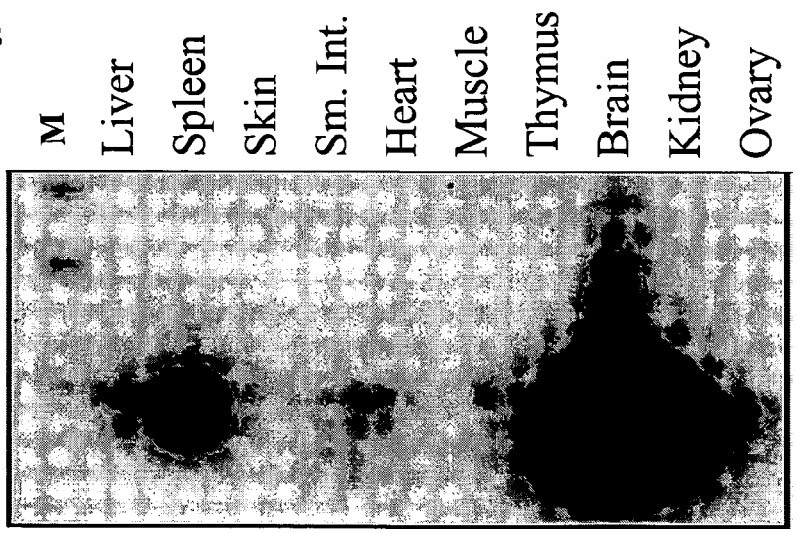

SEQUENCE LISTING

```
<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<223> OTHER INFORMATION: PCR primer

<400> SEQUENCE: 1
ctgctgggcg agcgggagac c                                    21

<210> SEQ ID NO 2
<211> LENGTH: 23
```

```
<212> TYPE: DNA
<213> ORGANISM: Artificial Sequence
<220> FEATURE:
<223> OTHER INFORMATION: PCR primer

<400> SEQUENCE: 2
gtggactaag acagttttct ggc                                    23

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
gaccctctcg gatcaccgcg c                                      21

<210> SEQ ID NO 4
<211> LENGTH: 21
<212> TYPE: DNA
<213> ORGANISM: Artificial Sequence
<220> FEATURE:
<223> OTHER INFORMATION: PCR primer

<400> SEQUENCE: 4
gtgagcaggt cagctagttg a                                      21

<210> SEQ ID NO 5
<211> LENGTH: 25
<212> TYPE: DNA
<213> ORGANISM: Artificial Sequence
<220> FEATURE:
<223> OTHER INFORMATION: PCR primer

<400> SEQUENCE: 5
aagagactct ggactattgg aagtg                                  25

<210> SEQ ID NO 6
<211> LENGTH: 25
<212> TYPE: DNA
<213> ORGANISM: Artificial Sequence
<220> FEATURE:
<223> OTHER INFORMATION: PCR primer

<400> SEQUENCE: 6
gcagatcaca catggttcga tggca                                  25

<210> SEQ ID NO 7
<211> LENGTH: 32
<212> TYPE: DNA
<213> ORGANISM: Artificial Sequence
<220> FEATURE:
<223> OTHER INFORMATION: PCR primer

<400> SEQUENCE: 7
cctaaaaatg gcaatattgt tcacggcaag ac                          32

<210> SEQ ID NO 8
<211> LENGTH: 32
<212> TYPE: DNA
<213> ORGANISM: Artificial Sequence
<220> FEATURE:
<223> OTHER INFORMATION: PCR primer

<400> SEQUENCE: 8
```

```
gtcttgccgt gaacaatatt gccattttta gg                                    32
```

```
<210> SEQ ID NO 9
<211> LENGTH: 21
<212> TYPE: DNA
<213> ORGANISM: Artificial Sequence
<220> FEATURE:
<223> OTHER INFORMATION: PCR primer

<400> SEQUENCE: 9
ccaatccaaa tgattgtgct a                                                21

<210> SEQ ID NO 10
<211> LENGTH: 21
<212> TYPE: DNA
<213> ORGANISM: Artificial Sequence
<220> FEATURE:
<223> OTHER INFORMATION: PCR primer

<400> SEQUENCE: 10
cattgttcct tagcaggctc c                                                21

<210> SEQ ID NO 11
<211> LENGTH: 695
<212> TYPE: DNA
<213> ORGANISM: Mus musculus
<220> FEATURE:
<221> NAME/KEY: 5'UTR
<222> LOCATION: (1)..(23)

<400> SEQUENCE: 11
ttctcctgcg ggcctccagg ccaatgtgca ataccaacat gtctgtgtct accgagggtg      60
ctgcaagcac ctcacagatt ccagcttcgg aacaagagac tctggactat tggaagtgta    120
cctcatgcaa tgaaatgaat cctccccttc catcacactg caaaagatgc tggacccttc    180
gtgagaactg gcttccagac gataagggga agataaagt ggaaatctct gaaaaagcca     240
aactggaaaa ctcagctcag gcagaagaag gcttggatgt gcctgatggc aaaaagctga    300
cagagaatga tgctaaagag ccatgtgctg aggaggacag cgaggagaag gccgaacaga    360 cgccccctgtc ccaggagagt gacgactatt cccaaccatc gacttccagc agcattgttt    420
atagcagcca agaaagcgtg aaagagttga aggaggaaac gcaggacaaa gacgagagtg    480
tggaatctag cttctcccctg aatgccatcg aaccatgtgt gatctgccag ggcggcccta   540
aaaatggctg cattgttcac ggcaagactg gacacctcat gtcatgtttc acgtgtgcaa    600
agaagttaaa aaaaagaaac aagccctgcc cagtgtgcag acagccaatc caaatgattg    660
tgctaagtta cttcaactag ctgacctgct cacaa                                695

<210> SEQ ID NO 12
<211> LENGTH: 217
<212> TYPE: PRT
<213> ORGANISM: Mus musculus

<400> SEQUENCE: 12

Met Cys Asn Thr Asn Met Ser Val Ser Thr Glu Gly Ala Ala Ser Thr
1               5                   10                  15

Ser Gln Ile Pro Ala Ser Glu Gln Glu Thr Leu Asp Tyr Trp Lys Cys
            20                  25                  30

Thr Ser Cys Asn Glu Met Asn Pro Pro Leu Pro Ser His Cys Lys Arg
        35                  40                  45

Cys Trp Thr Leu Arg Glu Asn Trp Leu Pro Asp Asp Lys Gly Lys Asp
```

-continued

```
                50                  55                  60
Lys Val Glu Ile Ser Glu Lys Ala Lys Leu Glu Asn Ser Ala Gln Ala
 65                  70                  75                  80

Glu Glu Gly Leu Asp Val Pro Asp Gly Lys Lys Leu Thr Glu Asn Asp
                 85                  90                  95

Ala Lys Glu Pro Cys Ala Glu Asp Ser Glu Lys Ala Glu Gln
                100                 105                 110

Thr Pro Leu Ser Gln Glu Ser Asp Asp Tyr Ser Gln Pro Ser Thr Ser
                115                 120                 125

Ser Ser Ile Val Tyr Ser Ser Gln Glu Ser Val Lys Glu Leu Lys Glu
            130                 135                 140

Glu Thr Gln Asp Lys Asp Glu Ser Val Glu Ser Ser Phe Ser Leu Asn
145                 150                 155                 160

Ala Ile Glu Pro Cys Val Ile Cys Gln Gly Arg Pro Lys Asn Gly Cys
                165                 170                 175

Ile Val His Gly Lys Thr Gly His Leu Met Ser Cys Phe Thr Cys Ala
            180                 185                 190

Lys Lys Leu Lys Lys Arg Asn Lys Pro Cys Pro Val Cys Arg Gln Pro
        195                 200                 205

Ile Gln Met Ile Val Leu Ser Tyr Phe
    210                 215
```

<210> SEQ ID NO 13
<211> LENGTH: 657
<212> TYPE: DNA
<213> ORGANISM: Homo sapiens

<400> SEQUENCE: 13

```
atgtgcaata ccaacatgtc tgtacctact gatggtgctg taaccacctc acagattcca      60
gcttcggaac aagagaccct ggactattgg aaatgcactt catgcaatga atgaatccc      120
ccccttccat cacattgcaa cagatgttgg gcccttcgtg agaattggct tcctgaagat     180
aaagggaaag ataagggga atctctgag aaagccaaac tggaaaactc aacacaagct       240
gaagagggct ttgatgttcc tgattgtaaa aaactatag tgaatgattc cagagagtca      300
tgtgttgagg aaaatgatga taaaattaca caagcttcac aatcacaaga agtgaagac      360
tattctcagc catcaacttc tagtagcatt atttatagca gccaagaaga tgtgaaagag     420
tttgaaaggg aagaaaccca agacaaagaa gagagtgtgg aatctagttt gcccttaat     480
gccattgaac cttgtgtgat tgtcaaggt cgacctaaaa atggttgcat tgtccatggc     540
aaaacaggac atcttatggc ctgctttaca tgtgcaaaga gctaaagaa aggaataag      600
ccctgcccag tatgtagaca accaattcaa atgattgtgc taacttattt ccccctag     657
```

<210> SEQ ID NO 14
<211> LENGTH: 217
<212> TYPE: PRT
<213> ORGANISM: Homo sapiens

<400> SEQUENCE: 14

```
Met Cys Asn Thr Asn Met Ser Val Pro Thr Asp Gly Ala Val Thr Thr
  1               5                  10                  15

Ser Gln Ile Pro Ala Ser Glu Gln Glu Thr Leu Asp Tyr Trp Lys Cys
                20                  25                  30

Thr Ser Cys Asn Glu Met Asn Pro Pro Leu Pro Ser His Cys Asn Arg
            35                  40                  45
```

```
Cys Trp Ala Leu Arg Glu Asn Trp Leu Pro Glu Asp Lys Gly Lys Asp
    50                  55                  60

Lys Gly Glu Ile Ser Glu Lys Ala Lys Leu Glu Asn Ser Thr Gln Ala
65                  70                  75                  80

Glu Glu Gly Phe Asp Val Pro Asp Cys Lys Lys Thr Ile Val Asn Asp
                85                  90                  95

Ser Arg Glu Ser Cys Val Glu Glu Asn Asp Asp Lys Ile Thr Gln Ala
            100                 105                 110

Ser Gln Ser Gln Glu Ser Glu Asp Tyr Ser Gln Pro Ser Thr Ser Ser
            115                 120                 125

Ser Ile Ile Tyr Ser Ser Gln Glu Asp Val Lys Glu Phe Glu Arg Glu
    130                 135                 140

Glu Thr Gln Asp Lys Glu Glu Ser Val Glu Ser Ser Leu Pro Leu Asn
145                 150                 155                 160

Ala Ile Glu Pro Cys Val Ile Cys Gln Gly Arg Pro Lys Asn Gly Cys
                165                 170                 175

Ile Val His Gly Lys Thr Gly His Leu Met Ala Cys Phe Thr Cys Ala
            180                 185                 190

Lys Lys Leu Lys Lys Arg Asn Lys Pro Cys Pro Val Cys Arg Gln Pro
            195                 200                 205

Ile Gln Met Ile Val Leu Thr Tyr Phe
    210                 215

<210> SEQ ID NO 15
<211> LENGTH: 25
<212> TYPE: DNA
<213> ORGANISM: Artificial Sequence
<220> FEATURE:
<223> OTHER INFORMATION: siRNA for knocking out Mdm2-b

<400> SEQUENCE: 15
ggaacaagag actctggact attgg                                   25
```

MDM2 SPLICE VARIANTS

CLAIM OF PRIORITY

This application claims priority under 35 USC §119(e) to U.S. patent application Ser. No. 60/517,318, filed on Nov. 3, 2003, the entire contents of which are hereby incorporated by reference.

FEDERALLY SPONSORED RESEARCH OR DEVELOPMENT

This invention was made with Government support under Grant No. 1R01CA077735-01A1 awarded by the National Cancer Institute. The Government has certain rights in the invention.

TECHNICAL FIELD

This invention relates to splice variants of Mdm2, and more particularly to a variant referred to herein as Mdm2-b.

BACKGROUND

The mouse double minute-2 gene (Mdm2) was initially identified in a screen for genes amplified on double minute chromosomes found in spontaneously transformed BALB/c 3T3 cells (Cahilly-Snyder et al., Somat. Cell Mol. Genet. 13:235-244 (1987)). When overexpressed, the Mdm2 has been demonstrated to immortalize rodent primary fibroblasts, to increase the rate of cellular proliferation, and to induce cellular transformation (Finlay, Mol. Cell Biol. 13:301-306 (1993)).

The human homolog, Hdm2, is an oncogene that is amplified in approximately one-third of human sarcomas and is overexpressed in a wide variety of other human cancers, including osteosarcomas, malignant fibrous histiocytomas, rhabdomyosarcomas, liposarcomas, leiomyosarcomas, glioblastomas, astrocytomas, myeloid leukemias, B-cell lymphomas, and oral squamous cell carcinomas (Oliner et al., Nature 358:80-83 (1992), Reifenberger et al., Cancer Res. 53:2736-2739 (1993), Bueso-Ramos, Blood 82:2617-2623 (1993), and reviewed in Bartel, Cell 2:9-15 (2002)). Given that p53 is perhaps the most commonly mutated gene in human cancers, and the absence of p53 mutations in many sarcomas that display Hdm2 amplification (Oliner et al., supra), it is likely that Hdm2-mediated inhibition of p53 is an important mechanistic step in the generation of these tumors, and overexpression of Hdm2 serves to inactivate p53 function in these tumors. Tumors have been identified that have both Hdm2 amplification and p53 loss (Cordon-Cardo et al., Cancer Res. 54: 794-799 (1994)). These rare sarcomas are much more aggressive than those tumors with alterations in only one of Fdm2 or p53, suggesting a p53-independent role for Hdm2 in these tumors.

Previous reports of analysis of a variety of human tumors that overexpress Hdm2 describe multiple, alternatively spliced forms of the Hdm2 message (Bartel et al., Int. J. Cancer 95:168-175 (2001)). In some cases, the presence of these spliced Hdm forms has been correlated with a more aggressive disease state (Matsumoto et al., Cancer Res. 58:609-613 (1998); Bartel et al., Cancer Cell 2:9-15 (2002)). Some of these transcripts encode Hdm2 proteins that lack the p53-binding domain and are incapable of complexing with p53, yet can induce foci formation in 3T3 cells in culture, suggesting that these tumor-isolated Hdm2 isoforms may contribute to transformation in a p53-independent manner (Sigalas et al., Nat. Med. 2:912-917 (1996)). Several spliced isoforms of Mdm2 and Hdm2 transcripts isolated from mouse or human tumors have been characterized, and many of these isoforms appear to inhibit cell proliferation, though the precise mechanism of growth inhibition remains unclear (Dang et al., Cancer Res. 62:1222-1230 (2002); Evans et al., Oncogene 20:4041-4049 (2001)).

SUMMARY

The present invention is based, at least in part, on the discovery of several alternative splice forms of Mdm2 transcripts from sarcomas that spontaneously arise in Mdm2-overexpressing mice. These transcripts include the mouse Mdm2-b, which is analogous to the splice form most commonly observed in human cancers (Hdm2-b). As shown herein, transduction of Mdm2-b into a variety of cells promotes cell growth and suppresses apoptosis. Furthermore, expression of Mdm2-b induces tumor formation in transgenic mice. Mdm2-b does not alter p53 stability, but increases the level of the anti-apoptotic, RelA (p65) protein and upregulates NFκB-mediated gene expression. These results indicate that an alternate spliced form of Mdm2 can contribute to formation of cancer via a p53-independent mechanism, and provides a rationale for the poorer prognosis of those patients presenting with tumors harboring multiple Hdm2 transcripts.

In one aspect the invention features isolated Mdm2-b nucleic acids and polypeptides. In one embodiment, the invention includes isolated nucleic acid molecules that encode an Mdm2-b polypeptide including an amino acid sequence of SEQ ID NO:12, or a polypeptide including an amino acid sequence of SEQ ID NO:12 with one or more conservative amino acid substitutions, e.g., that can inhibit apoptosis in a cell, In some embodiments, the invention includes isolated nucleic acid molecule having or including a nucleotide sequence of SEQ ID NO: 11. In addition, the invention provides expression vectors including the isolated nucleic acid sequences described herein, and host cells including the expression vectors described herein. The invention also includes isolated Mdm2-b polypeptides having an amino acid sequence of SEQ ID NO:12 or an amino acid sequence of SEQ ID NO:12 with one or more conservative amino acid substitutions, that can inhibit apoptosis in a cell. (In some embodiments, the isolated Mdm2-b polypeptides having one or more conservative amino acid substitutions have one or more activities of the natural Mdm2-b, e.g., NFkB-induced gene expression, the ability to inhibit apoptosis in a cell in the absence of functional p53. In some embodiments, the level of activity of the polypeptides having one or more conservative amino acid substitutions is at least 35%, e.g., at least 50%, 75%, or 90%, that of the natural polypepride.

The invention also provides antibodies that bind specifically to the isolated Mdm2-b polypeptide described herein, e.g., antibodies that do not bind substantially to wild-type Mdm2.

Also provided herein are methods of screening test compounds. The methods include providing a cell expressing an Mdm2-b polypeptide; contacting the cell with the test compound; and evaluating an effect of the test compound on expression or activity of the Mdm2-b polypeptide in the cell, thereby screening the test compound. The test compound can be, e.g., an antisense molecule, siRNA, ribozyme, or antibody that binds specifically to the Mdm2-b polypeptide, or a small molecule. In some embodiments, the effect is a decrease in Mdm2 expression or activity.

In addition, the invention provides methods for identifying candidate compounds for the treatment of cancer. The methods include providing a sample comprising a cell expressing an Mdm2-b polypeptide; contacting the sample with a test compound; and evaluating one or more of expression or activity of the Mdm2-b polypeptide in the sample. A decrease in the expression or activity of the Mdm2-b polypeptide in the sample in the presence of the test compound, as compared to a reference (e.g., a control sample in the absence of the test compound), indicates that the test compound is a candidate compound for the treatment of cancer. In some embodiments, the cell expresses nuclear factor κB (NFκB) and can support NFκB-induced gene expression; in some embodiments, NFkB-induced gene expression is reduced in the presence of the test compound.

In some embodiments, the evaluating step comprises monitoring cell proliferation in the presence of the test compound. In some embodiments, cell proliferation is reduced in the presence of the test compound.

Further, the invention provides methods for identifying candidate agents for the treatment of cancer. The methods include providing a cell or animal model of cancer; contacting the model with a candidate compound that decreases the expression or activity of Mdm2-b (e.g., a candidate compound identified by a method described herein; and evaluating the effect of the test compound on one or more parameters of cancer in the model. An improvement in a parameter indicates that the compound is a candidate agent for the treatment of cancer.

In some embodiments, the model is an animal model and the parameter is, e.g., one or more of tumor size, tumor number, tumor growth rate, age at appearance of first tumor, and mortality rate. In some embodiments, the animal model is an Mdm2-b transgenic animal, at least some of whose somatic and germ cells include a transgene encoding an Mdm2-b polypeptide having an amino acid sequence of SEQ ID NO:12, e.g., as described herein.

In some embodiments, the model is a cell model and the parameter is, e.g., one or more of cell viability and cell proliferation.

The invention also provides methods for treating cancer in a subject, by identifying a subject having a tumor, wherein the tumor has increased nuclear factor kB (NFkB) expression or activity; and administering to the subject a therapeutically effective amount of a composition comprising an agent that decreases the expression or activity of Hdm2 or a variant thereof, e.g., an agent identified by a method described herein.

Also provided herein are methods for selecting a candidate subject for treatment with an agent that reduces expression or activity of an Hdm2-b polypeptide. The methods include identifying a subject having a tumor; obtaining a sample from the subject comprising cells from the tumor; and determining a level of NFκB activity or expression in the cells. An increase in the level relative to a reference indicates that the subject is a candidate subject for treatment with an agent that reduces expression or activity of an Hdm2-b polypeptide. In some embodiments, the method further includes administering to the subject an agent that reduces expression or activity of an Hdm2-b polypeptide, e.g., an agent identified by a method described herein.

The level of NFkB activity or expression can be determined by measuring NFκB protein levels using antibodies specific for NFκB (e.g., antibodies specific for a p50 or p65 subunit of NFκB) or by measuring NFκB activity using an NFκB reporter gene assay.

The invention also includes transgenic animals, e.g., transgenic mice, at least some of whose somatic and germ cells have a transgene encoding a variant of Mdm2, e.g., Mdm2-b. In some embodiments, the somatic and germ cells have two copies of the transgene. Also provided are isolated cells derived from the transgenic animals, e.g., fibroblasts or mouse embryonic fibroblasts (MEFs).

Further, the invention provides vectors suitable for expressing an Mdm2 variant transgene in a transgenic animal, e.g., vectors comprising a GFAP promoter.

In a further aspect, the invention features methods for screening test compounds. The methods include administering the test compound to an Mdm2-b transgenic animal as described herein; and evaluating an effect of the test compound on the animal, thereby screening the compound. In some embodiments, the animal has a tumor, and the effect that is evaluated is an effect on the tumor, e.g., the size, growth rate, or metastasis of the tumor. In some embodiments, the animal does not have any tumors, and the effect that is evaluated is an effect on the development of tumors, e.g., a delay in, or prevention of, the development of tumors.

In another aspect, the invention provides anti-Mdm2 variant-specific antibodies.

The invention provides several advantages. Splice variants of the Hmd2 gene, including the human homolog of the Mdm2-b variant, Hdm2-b, are expressed in a number of human tissues and can be used to produce the vectors, animals, and cells described herein. The animals and cells described herein are particularly useful, e.g., as models of tumors in which Mdm2-b or Hdm2-b is expressed at high levels, and can be used in screening for modulators, e.g., therapeutic compounds for use in the treatment of disorders associated with cell proliferation, e.g., cancer. In particular, the animals and cells described herein, e.g., Mdm2-b expressing transgenic animals and cells, provide the advantage of a model of Mdm2 action that is independent of p53.

As used herein, the term "nucleic acid molecule" includes DNA molecules (e.g., a cDNA) and RNA molecules (e.g., an mRNA) and analogs of the DNA or RNA generated, e.g., by the use of nucleotide analogs. The nucleic acid molecule can be single-stranded or double-stranded, but typically is double-stranded DNA.

The term "isolated or purified nucleic acid molecule" includes nucleic acid molecules that are separated from other nucleic acid molecules that are present in the natural source of the nucleic acid. For example, in various embodiments, the isolated nucleic acid molecule can contain less than about 0.1 kb of 5' and/or 3' untranslated nucleotide sequences that naturally flank the nucleic acid molecule, e.g., in the mRNA. Moreover, in some embodiments, an "isolated" nucleic acid molecule, such as a cDNA molecule, is substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent conditions are known to those skilled in the art and can be found in *Current Protocols in Molecular Biology*, John Wiley & Sons, N.Y. (1989), 6.3.1-6.3.6. Aqueous and nonaqueous methods are described in that reference and either can be used. As used herein, stringency conditions are 0.5 M sodium phosphate, 7% SDS at 65° C., followed by one or more washes at 0.2×SSC, 1% SDS at 65°

C. An isolated nucleic acid molecule as described herein that hybridizes under stringent conditions to the sequence of SEQ ID NO:11 is an Mdm2 variant.

As used herein, a "naturally-occurring" nucleic acid molecule refers to an RNA or DNA molecule having a nucleotide sequence that occurs in nature (e.g., a wild type sequence that encodes a natural protein).

As used herein, the terms "gene" and "recombinant gene" refer to nucleic acid molecules that include an open reading frame encoding an Mdm2 variant protein, typically a mammalian Mdm2 variant protein, and can further include non-coding regulatory sequences, and introns.

The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments that can be generated by treating the antibody with an enzyme such as pepsin.

"Subject," as used herein, can refer to a mammal, e.g., a human, or to an animal or animal model. The subject can also be a domesticated animal, e.g., a horse, cow, goat, dog, cat, pig, or primate.

A "purified preparation of cells," as used herein, refers to, in the case of plant or animal cells, an in vitro preparation of cells and not an entire intact plant or animal. In the case of cultured cells or microbial cells, it consists of a preparation of at least about 50% of the subject cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1A is a photograph of a gel showing nested PCR products generated from Mdm2-transgenic mouse tumor numbers 20, 103, 186, 238, 98, and 110. Wildtype tissue (wt) sample and marker (M) are on right.

FIG. 1B is a photograph of a gel showing that Mdm2-b is present in all tumor samples analyzed. Top panel, Mdm2-b isoform-specific primers were used to amplify tumor cDNAs; Bottom panel, GAPDH PCR was used as a control to confirm the presence of intact cDNA.

FIG. 1C is an amino acid sequence alignment of the mouse Mdm2-b (SEQ ID NO: 12) and human Hdm2-b (SEQ ID NO:14). The two proteins share approximately 82-84% amino acid identity. The boxed cysteine residue at amino acid 176 was mutated to arginine (C176N) to generate the RING finger mutant Mdm2-b$^{ssp1}$. Triangles=exon 3–exon 12 splice site.

FIG. 1D is a representation of a blot showing that in vitro transcription and translation of Xpress-Mdm2-b and Xpress-Mdm2-bSsp1 produces a 47 kDa protein (minus the 3.5 kDa Xpress epitope).

FIG. 1E is a photomicrograph showing the results of immunolocalization using DAPI for nuclear staining and FITC-Anti-Xpress Antibody for detection of Xpress-Mdm2-b, revealing that Mdm2-b is localized predominantly in the cytoplasm (triangles, top panel). Xpress-AML3 was used as a positive control for nuclear localization (triangle, lower panel).

FIG. 2A is a scatter plot showing that transduction of Mdm2-b or Hdm2-b increases the growth rate of NIH3T3 cells as evidenced by an increase in BrdU staining.

FIG. 2B is a line graph showing that the RING finger of Mdm2-b increases the percentage of asynchronous NIH3T3 cells undergoing DNA replication.

FIG. 2C is a line graph demonstrating that Mdm2-b and Hdm2-b increases the proliferation of low-passage, p53-deficient MEFs.

FIG. 2D is a line graph demonstrating that that Mdm2-b increases the proliferation of low-passage, p53-deficient MEFs, whereas Mdm2-b bearing a mutation in the RING finger is less able to stimulate cell growth.

FIG. 2E is a bar graph illustrating that transduction of the B isoform into Rb-deficient MEFs or p19(ARF)-deficient MEFs increases cell growth. The average cell numbers and standard deviations of triplicate plates of cells are given at Time 0 and 120 hours.

FIG. 4A is a schematic illustration of the β-actin-Mdm2-b and GFAP-Mdm2-b transgene constructs used in pronuclear injection experiments.

FIG. 4B is a representation of a Southern blot showing the results of analysis of transgene expression in multiple tissues of a representative GFAP-Mdm2-b transgenic mouse by RT-PCR followed by Southern analysis with an Mdm2-B specific oligonucleotide probe. High levels of transgene expression were seen in brain, spleen, and liver, with lesser levels of expression in other tissues.

DETAILED DESCRIPTION

Figure 3A:
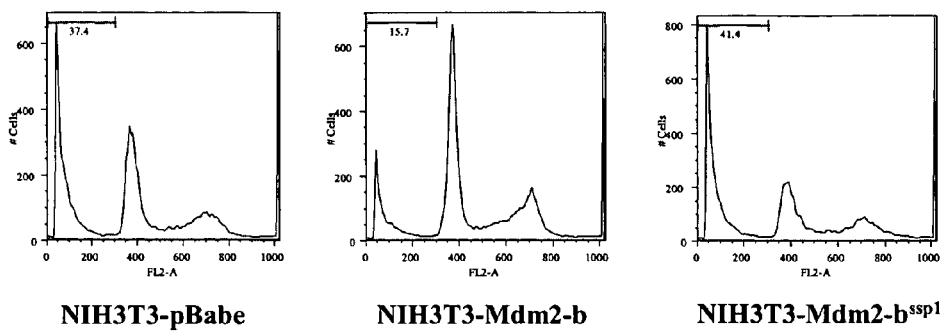
FIG. 3A is a series of graphs illustrating the results of an experiment in which NIH3T3 cells transduced with empty vector pBabe, Mdm2-b or Mdm2-b Ssp1 were examined for their response to doxorubicin-induced apoptosis. Sub-confluent cells were treated with doxorubicin and analyzed for sub-G0 DNA content by FACS analysis. The percentage of cells showing DNA fragmentation is given for each sample.

To assess the potential role of Mdm2 isoforms in tumorigenesis, sarcomas isolated from Mdm2-overexpressing transgenic mice were analyzed. As described herein, numerous new spliced isoforms of Mdm2 transcripts were detected in the tumors, including the murine equivalent of the B isoform; the most prevalent isoform observed in human cancers. The human double minute-2 B isoform, Hdm2-b, which has been previously detected in high-grade bladder and uterine cancers, lacks the p53-binding region present in full-length Hdm2 and is incapable of complexing with the p53 protein (Sigalas et al., Nat. Med. 2:912-917 (1996)). Hdm2-b is the most commonly observed isoform in human cancers that overexpress Hdm2. The functional significance of the murine Mdm2-b form was evaluated in cells and in mice; the results, described herein, indicate that this isoform encodes a variant Mdm2 protein. Mdm2-b, like Hdm2-b, is generated by precise splicing between exon 3 and 12 of the Mdm2 gene and maintains the reading frame of the protein. The Mdm2-b alternate transcript encodes a 47 kD protein that lacks the nuclear localization signal found on full-length Mdm2 and was determined to localize to the cytoplasmic compartment. Like Hdm2-b, Mdm2-b lacks the p53-binding domain and contains only the carboxy-terminal RING domain. Mdm2-b and Hdm2-b proteins share 82% amino acid identity; given this, it is expected that compounds that affect Mdm2-b expression or activity will similarly affect Hdm2-b expression or activity, making Mdm2-b a useful proxy for Mdm2-b, particularly in murine animal models.

This variant Mdm2 protein induces cell proliferation and interferes with apoptosis in a p53-independent manner in cultured cells, and induces spontaneous tumorigenesis in transgenic mice. Mdm2-b increases the level of the RelA (p65) protein in cells and in mice, and Mdm2-b can increase NFκB-dependent transcription in transduced cells and potentiate the response of these cells to TNF-mediated apoptosis. These results identify a p53-independent role for Mdm2 in cell proliferation and apoptosis, and demonstrate that a splice isoform of Mdm2 can induce tumor formation in vivo. Thus, as one theory, not meant to be limiting, the presence of increased levels of this splice isoform of Mdm2 contributes to the neoplasia induced by Mdm2 overexpression in human cancers.

Mdm2-b increases the proliferation of transduced NIH3T3 cells without altering p53 stability in the cells, and transduction of Mdm2-b increases the proliferation of p53-null MEFs, as well as Rb-null MEFs and p19(ARF)-null MEFs. These results indicate that Mdm2-b increases cell proliferation via a p53-independent mechanism that furthermore does not require the presence of RB or p19(ARF) to function. In addition, Mdm2-b interferes with cell death, and can induce foci formation in cultured cells, indicating that Mdm2-b has oncogenic potential, as was confirmed by the results of the transgenic study.

Expression of Mdm2-b in transgenic mice induced spontaneous tumor formation in myeloid progenitor cells and B lymphocytes, possibly due to the choice of promoter used in construction of the transgene; the Glial Fibrillary Acidic Protein (GFAP) promoter induced the highest levels of Mdm2-b expression in the brain, with a lesser amount of expression in the spleen in all three lines of transgenic mice. Although a subset of the Mdm2-b transgenic mice suffered lethality resulting from hydrocephaly or exhibited an aberrant gait, no tumors were detected in brain tissue of Mdm2-b transgenic mice.

While the precise mechanism(s) for Mdm2-b-induced tumor formation is uncertain, it is likely to be independent of p53, as Mdm2-b neither binds to p53 nor requires the presence of functional p53 to increase cell proliferation. As one theory, not meant to be limiting, Mdm2-b may induce tumorigenesis, in part, by altering NFκB activity in the cell. Many tumor cell lines, including myeloid and lymphoma cells, have been found to express constitutively active NFκB (reviewed in Richmond, Nat. Rev. Immunol. 2:664-674 (2002)), and NFκB has also been observed to be upregulated in primary tumor samples (Garg and Aggarwal, Leukemia 16:1053-68 (2002)). Expression of Mdm2-b induces RelA, the anti-apoptotic NFκB subunit (also referred to herein as p65), in both transduced cells and in tumor tissues isolated from the transgenic mice. Furthermore, Mdm2-b was capable of increasing NFκB-dependent transcription and potentiating the effects of TNF-alpha on RelA-mediated transcription in transfected cells.

Induction of p53 activates NFκB and correlates with the ability of p53 to induce apoptosis (Ryan et al., Nature 404:892-897 (2000)). However, using a p53-inducible, Saos-2 cell system, expression of RelA in cells was found to protect cells from TNF-alpha-induced death without significantly altering p53-induced apoptosis. This suggests that induction of RelA and inhibition of cell death by the Mdm2-b isoform in our experiments is unlikely to affect p53-mediated apoptosis, in agreement with our proposal for a p53-independent mechanism for Mdm2-b induced tumorigenesis. In addition, NFκB has been implicated in upregulation of other cell cycle regulatory genes with potential oncogenic functions (Karin et al., Nat. Rev. Cancer 2:301-310 (2002)).

The oncogenic effects of Hdm2-b may require the RING domain, because substitution of a single cysteine residue critical to formation of the $Zn^{++}$ finger structure (Fang et al., J. Biol. Chem. 275:8945-8951 (2000)) diminishes the pro-proliferative effects and abolishes the anti-apoptotic effects of Hdm2-b. As one non-limiting theory, Mdm2 may act as a transcription factor, binding to SP1 sites present in the RelA promoter and inducing RelA expression (Gu and Zhou, Blood 99:3367-3375 (2002)). Given the cytoplasmic location of Mdm2-b and the lack of an acidic activating domain, it is unlikely that Mdm2-b is altering RelA expression directly.

A p53-independent role for Mdm2-b/Hdm2-b in cell growth and death has significant clinical importance. Not only do these results provide a rationale for the poorer prognosis of those patients presenting with tumors harboring multiple Hdm2 transcripts, but the full-length protein also contains all of the sequences present on the isoform. Thus, any p53-independent functions for Hdm2-b also likely exist for Hdm2 itself, suggesting that the use of small molecule inhibition to restore functional p53 in tumors with increased Hdm2 expression levels may not be sufficient to ameliorate all of the tumorigenic effects of Hdm2.

Mouse Mdm2 Variant Polypeptides

The invention includes isolated polypeptides comprising naturally-occurring Mdm2 splice variants. An Mdm2 variant polypeptide can include one or more of the following: a p19(ARF) binding domain, an ATM-induced phosphorylation site, and a Zinc-RING domain. In some embodiments, the presence of such a domain can be verified by any means known in the art, e.g., using an algorithm, e.g., a computer-based algorithm. For example, to identify the presence of a domain, e.g., a Zinc-RING finger domain, in an Mdm2 variant protein sequence, and to make the determination that a polypeptide or protein of interest has a particular profile, the amino acid sequence of the protein can be searched against a structural database, e.g., the Pfam database, SMART database (Simple Modular Architecture Research Tool), or ProDom (Corpet et al. (1999), Nucl. Acids Res. 27:263-267), using the default parameters (e.g., as available on the internet).

As the Mdm2 variant polypeptides described herein may modulate Mdm2 variant-mediated activities (e.g., cell proliferation), they may be useful for developing novel diagnostic and therapeutic agents for Mdm2 variant-mediated or related disorders, as described below.

As used herein, an "Mdm2 variant activity," "biological activity of Mdm2 variant," or "functional activity of Mdm2 variant," refers to an activity exerted by an Mdm2 variant protein, polypeptide, or nucleic acid molecule on, e.g., an Mdm2 variant-responsive cell or on an Mdm2 variant substrate, e.g., a protein substrate, as determined in vivo or in vitro. In one embodiment, an Mdm2 variant activity is a direct activity, such as an association with an Mdm2 variant binding partner. A "binding partner" is a molecule with which an Mdm2 variant protein binds or interacts in nature, e.g., p19(ARF).

An Mdm2 variant activity can also be an indirect activity, e.g., a cellular signaling activity mediated Mdm2, e.g., by interaction of the Mdm2 variant protein with an Mdm2 binding partner. The Mdm2 variant molecules described herein have one or more of the biological activities of the full-length Mdm2, or can interfere with one or more biological activities of the full length Mdm2. For example, an Mdm2 variant polypeptide has one or more of the following activities: E3 ligase, and p19(ARF) binding. An Mdm2 variant can cause one or more of the following: increased cell proliferation; decreased cell proliferation; or decreased p53 levels. In one embodiment, an Mdm2 variant activity is induction of NFκB activity, e.g. NFκB-mediated gene expression.

Thus, the Mdm2 variant molecules (e.g., polypeptides or nucleic acids) can act as novel diagnostic targets and therapeutic agents for controlling disorders associated with excessive cell proliferation, e.g., cancer (e.g., carcinoma, sarcoma, metastatic disorders or hematopoietic neoplastic disorders, e.g., leukemias) or skin proliferative disorders such as psoriasis. Metastatic tumors can arise from a multitude of primary tumor types, including, but not limited to, those of the lung, breast, liver, thyroid, lymphoid, gastrointestinal, and genito-urinary tract, as well as adenocarcinomas that include malignancies such as most colon cancers, renal-cell carcinoma, prostate cancer and/or testicular tumors, non-small cell carcinoma of the lung, cancer of the small intestine and cancer of the esophagus.

As used herein, the terms "cancer," "hyperproliferative," and "neoplastic" refer to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness, including, but not limited to, carcinomas, sarcomas, carcinosarcomas, and adenosarcomas.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof.

The Mdm2 variant protein, fragments thereof, and derivatives and other variants of the sequence in SEQ ID NO:12 thereof are collectively referred to as "Mdm2 variant polypeptides" or "Mdm2 variant proteins." Nucleic acid molecules encoding such polypeptides or proteins are collectively referred to as "Mdm2 variant nucleic acids." Mdm2 variant molecules refer to Mdm2 variant nucleic acids, polypeptides, and antibodies.

In some embodiments, the Mdm2 variant polypeptide is an Mdm2-b polypeptide. An Mdm2-b polypeptide according to the invention is substantially identical to, e.g., at least about 85% identical to, the amino acid sequence of SEQ ID NO:12. In some embodiments, an Mdm2-b polypeptide is at least about 90%, 95%, 99%, or 100% identical to the Mdm2-b variant described herein (e.g., SEQ ID NO:12). Particular Mdm2 variant polypeptides described herein have an amino acid sequence substantially identical to the amino acid sequence of SEQ ID NO:12. The term "substantially identical" is used herein to refer to a amino acid or nucleotide sequences that are at least about 85% identical. In some embodiments, the amino acid or nucleotide sequences contain a common structural domain having at least about 90%, 91%, 92%, 93%, 94%, 95%, 96%, 97%, 98%, or 99% identity. Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In some embodiments, the length of a reference sequence aligned for comparison purposes is at least 80% of the length of the reference sequence, and in some embodiments it is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences is accomplished using the Needleman and Wunsch ((1970) J. Mol. Biol. 48:444-453) algorithm, which has been incorporated into the GAP program in the GCG software package (available on the world wide web at gcg.com), using a Blossum 62 scoring matrix with a gap penalty of 12, a gap extend penalty of 4, and a frameshift gap penalty of 5.

The invention also includes Mdm2 variants having one or more conservative amino acid substitutions, e.g., mutants of Mdm2-b having a conservative amino acid substitution useful in identifying regions important in biological function. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an Mdm2 variant protein is typically replaced with another amino acid residue from the same side chain family. Alternatively, in another embodiment, mutations can be introduced randomly along all or part of an Mdm2 variant coding sequence, such as by saturation mutagenesis, and the resultant mutants can be screened for Mdm2 variant biological activity to identify mutants that retain activity. Following mutagenesis, the encoded protein can be expressed recombinantly and the activity of the protein can be determined.

Mouse Mdm2 Variant Nucleic Acid Molecules

In one aspect, the invention provides an isolated or purified, nucleic acid molecule that encodes an Mdm2 variant polypeptide as described herein, e.g., a full length Mdm2 variant protein, or an active fragment thereof. Also included are nucleic acid fragments suitable for use as hybridization probes, which can be used, e.g., to identify nucleic acid molecules encoding a polypeptide described herein, Mdm2 variant mRNA, and fragments suitable for use as primers, e.g., PCR primers for the amplification or mutation of Mdm2 variant nucleic acid molecules.

In one embodiment, an isolated nucleic acid molecule described herein includes the nucleotide sequence of SEQ ID NO:11. In one embodiment, the nucleic acid molecule includes sequences encoding the human Mdm2 variant protein (i.e., "the coding region" of SEQ ID NO:11, nucleotides 24-695), as well as 5' untranslated sequences. Alternatively, the nucleic acid molecule can include only the coding region of SEQ ID NO:11 (e.g., nucleotides 24-695) and, e.g., no flanking sequences that normally accompany the subject sequence.

In another embodiment, the isolated nucleic acid molecules include a nucleic acid molecule that is a complement of the nucleotide sequence of SEQ ID NO:11, or a portion of any of these nucleotide sequences. In other embodiments, the new nucleic acid molecules are sufficiently complementary to the nucleotide sequence of SEQ ID NO:11 that they can hybridize under stringent conditions to the nucleotide sequence of SEQ ID NO:11, thereby forming a stable duplex.

In one embodiment, an isolated nucleic acid molecule described herein includes a nucleotide sequence that is at least about 85% or more identical to the entire length of the nucleotide sequence of SEQ ID NO:11. In some embodiments, the nucleotide sequence is at least about 90%, 91%, 92%, 93%, 94%, 95%, 96%, 97%, 98%, 99% or 100% identica SEQ ID NO:11.

The new nucleic acid molecules can include only a portion of the nucleic acid sequence of SEQ ID NO:11. For example, such a nucleic acid molecule can include a fragment that can be used as a probe or primer, e.g., a fragment directed to a sequence of a splice site not present in the full-length Mdm2.

Thus, probes and primers that specifically detect or amplify an Mdm2 variant are provided. Typically a probe/primer is an isolated or purified oligonucleotide. The oligonucleotide typically includes a region of nucleotide sequence that hybridizes under stringent conditions to at least about 25 consecutive nucleotides of a sense or antisense sequence of SEQ ID NO:11. In some embodiments, the oligonucleotide comprises about 30, 35, 40, 45, 50, 55, 60, 65, 75, 100, 150, 200, 300, 400, 500 or more consecutive nucleotides of SEQ ID NO:11.

In some embodiments, the nucleic acid is a probe that is at least 25, and less than about 200 (typically less than about 100 or 50), base pairs in length. It should be identical, or differ by 1, or less than 1 in 10 bases, from a sequence disclosed herein. If alignment is needed for this comparison the sequences should be aligned for maximum homology. "Looped" out sequences from deletions or insertions, or mismatches, are considered differences.

In another embodiment, a set of primers is provided, e.g., primers suitable for use in PCR, which can be used to amplify a selected region of an Mdm2 variant sequence, e.g., to detect the presence of a specific variant. The primers should be at least 20 base pairs in length and less than about 100 base pairs in length. The primers should be identical, or differ by less than one or two in 10 bases from a sequence disclosed herein or from a naturally occurring variant. For example, suitable primers include a first primer from a first portion of the sequence of the variant that is upstream of the splice site, and a second primer that is from a second portion of the sequence of the variant that is downstream of the splice site, such that amplification using these primers results in a PCR product that has a different size, depending on whether the template nucleic acid includes one or both of the full length Mdm2 and the Mdm2 variant.

Anti-Mdm2 Variant Antibodies

The anti-Mdm2 variant-specific antibodies described herein can be polyclonal, monoclonal, or monospecific. The antibodies can be recombinant, e.g., a chimeric or humanized, fully human, or non-human, e.g., murine, or single chain antibodies. In some embodiments they have effector function and can fix complement. The antibodies can be coupled to a toxin or imaging agent.

A full-length Mdm2 variant protein or antigenic peptide fragment of Mdm2 variant can be used as an immunogen or can be used to identify anti-Mdm2 variant antibodies made with other immunogens, e.g., cells, membrane preparations, and the like. The new antigenic peptides of Mdm2 variants should include at least 8 amino acid residues of the amino acid sequence shown in SEQ ID NO:12 and encompass an epitope of an Mdm2 variant that is specific for that variant. Typically, the antigenic peptide includes at least about 10, 15, 20, or 30 amino acid residues comprising the variant-specific epitope, e.g., residues comprising a splice site in a variant.

Fragments of an Mdm2 variant can be used, e.g., as immunogens to make antibodies against the Mdm2 variant protein or used to characterize the specificity of an antibody.

Antibodies reactive with, or specific for, any of these regions, or other regions or domains described herein are provided.

Typically, epitopes encompassed by the antigenic peptide are regions of Mdm2 variant located on the surface of the protein, e.g., hydrophilic regions, as well as regions with high antigenicity. For example, crystallographic structures of the wild-type Mdm2, or an Emini surface probability analysis of the human Mdm2 variant protein sequence, can be used to indicate the regions that have a particularly high probability of being localized to the surface of the Mdm2 variant proteins, and are thus likely to constitute surface residues useful for targeting antibody production.

The anti-Mdm2 variant antibodies can be single chain antibodies. A single-chain antibody (scFV) can be engineered using methods known in the art (see, for example, Colcher, et al., *Ann N Y Acad Sci* 880:263-80 (1999); and Reiter, *Clin. Cancer Res.* 2:245-52 (1996)). The single chain antibodies can be dimerized or multimerized to generate multivalent antibodies having specificities for different epitopes of the same target Mdm2 variant protein.

In some embodiments, the antibodies have a reduced or no ability to bind to an Fc receptor. For example, they can be an isotype or subtype, fragment, or other mutant, which does not support binding to an Fc receptor, e.g., they have a mutagenized or deleted Fc receptor binding region.

Anti-Mdm2 variant antibodies (e.g., monoclonal antibodies) can be used to isolate Mdm2 variant polypeptides by standard techniques, such as affinity chromatography or immunoprecipitation. Moreover, anti-Mdm2 variant antibodies can be used to detect Mdm2 variant protein (e.g., in a cellular lysate or cell supernatant) to evaluate the abundance and pattern of expression of the protein. Anti-Mdm2 variant antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Transgenic Animals, Vectors and Host Cells

A "transgenic animal" is a non-human animal, such as a mammal, generally a rodent such as a rat or mouse, in which one or more of the cells of the animal includes a transgene. Other examples of transgenic animals include non-human primates, sheep, dogs, cows, goats, chickens, amphibians, and the like. A "transgene" is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologously recombinant animal" is a non-human transgenic animal, such as a mammal, typically a mouse, in which an endogenous Mdm2 gene has been altered by homologous recombination between the endogenous gene and an exogenous DNA molecule introduced into a cell of the animal, e.g., an embryonic cell of the animal, prior to completed development of the animal. The transgene can lead to the expression of an Mdm2 variant, e.g., Mdm2-b, gene product in one or more cell types or tissues of the transgenic animal.

In some embodiments, the transgene is inducible, e.g., only expressed under selected circumstances, e.g., a transgene controlled by an inducible promoter. Alternatively, a conditional Mdm2 variant can be constructed, e.g., by inserting lox or FRT sequences appropriately so that the variant is produced in the presence of a recombinase, e.g., Cre or FLT, such that the portion of the gene that is missing in the variant is excised by the recombinase. "Suppression of gene expression" includes both complete suppression and partial suppression, suppression under specific circumstances, and suppression of one or both alleles of a gene. Expression can be monitored by any method known in the art, and can be measured by assaying RNA, protein, or activity.

A transgenic animal can be one in which an endogenous Mdm2 gene has been altered, e.g., by introduction of an exogenous DNA molecule (such as the Mdm2-b gene targeting vectors described herein) into a cell of the animal, e.g., an embryonic cell of the animal, prior to development of the animal. A line of transgenic animals (e.g., mice, rats, guinea pigs, hamsters, rabbits, or other mammals) can be produced bearing a transgene, e.g., a transgene encoding a variant of Mdm2, e.g., Mdm2-b.

Methods known in the art for producing transgenic animals can be used to generate an animal, e.g., a mouse, that bears one or more copies of an Mdm2 variant, e.g., Mdm2-b. In one embodiment, the animal bears only a single copy of the Mdm2 variant, e.g., a "heterozygous" animal. Two such heterozygous animals can be crossed to produce offspring that are homozygous for the variant allele.

For example, in one embodiment, an exogenous nucleic acid encoding a variant of Mdm2, e.g., Mdm2-b is introduced into a cell, e.g., a fertilized oocyte or an embryonic stem cell. Such cells can then be used to create non-human transgenic animals in which the Mdm2 variant sequences have been introduced into their genome, e.g., homologously recombinant animals whose genomes contain one or more exogenous Mdm2 variant nucleic acid sequences, e.g., Mdm2-b. Such animals are useful for studying the function and/or activity of Mdm2 variants, e.g., Mdm2-b, and for identifying and/or evaluating modulators of Mdm2 and/or p53 function, as well as the functional consequences of downregulating or eliminating Mdm2 activity in an adult animal.

Methods for generating transgenic animals, e.g., animals such as mice, via embryo manipulation and electroporation or microinjection of pluripotent stem cells or oocytes, are known in the art and are described, for example, in U.S. Pat. Nos. 4,736,866 and 4,870,009, U.S. Pat. No. 4,873,191, U.S. Ser. No. 10/006,611, and in Hogan, Manipulating the Mouse Embryo, (Cold Spring Harbor Laboratory Press, Cold Spring Harbor, N.Y., 1986), which are incorporated herein by reference in their entirety. Retroviral vectors can also be used, e.g., as described in Robertson et al., Nature 323:445-448 (1986). Retroviruses generally integrate into the host genome with no rearrangements of flanking sequences, which is not always the case when DNA is introduced by microinjection or other methods. Methods similar to those used to create transgenic mice can be used for production of other transgenic animals. A transgenic founder animal can be identified based upon the presence of the Mdm2 variant transgene in its genome, for example by detecting the presence of sequences unique to the variant, e.g., sequences spanning a splice site unique to that variant. Founder animals can also be identified by detecting the presence or expression of the gene product of the Mdm2 variant, e.g., Mdm2-b mRNA or polypeptide in tissues or cells of the animals. For example, fibroblasts can be used, such as embryonic fibroblasts or fibroblasts derived from the post-natal animal, e.g., the ear of the post-natal animal. A transgenic founder animal can then be used to breed additional animals carrying the transgene. Moreover, transgenic animals carrying a transgene encoding an Mdm2 variant can further be bred to other transgenic animals carrying other transgenes.

The vector can be introduced into an embryonic stem cell line (e.g., by electroporation), and cells in which the introduced Mdm2 variant sequence has homologously recombined with the endogenous Mdm2 gene are selected, e.g., by antibiotic selection (see, e.g., Li et al., Cell 69:915-926 (1992)). Selected cells are then injected into a blastocyst of an animal (e.g., a mouse) to form aggregation chimeras (see, e.g., Bradley, in *Teratocarcinomas and Embryonic Stem Cells: A Practical Approach*, Robertson, ed. (IRL, Oxford, 1987) pp. 113-152). A chimeric embryo can then be implanted into a pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, Current Opinion in Bio/Technology 2:823-829 (1991), and in PCT Publication Nos. WO 90/11354, WO 91/01140, WO 92/0968, and WO 93/04169. One method of producing such mice is described in Example 1 herein.

Host cells can be isolated from a transgenic animal using methods known in the art, or can be created by transfecting or transforming cells, such as primary or cultured cells, e.g., mammalian or non-mammalian fibroblasts, thymocytes, neurons, glia, or ES cells, inter alia, with the Mdm2 gene targeting vectors described herein using known methods. For example, vector DNA can be introduced into host cells via conventional transformation, transduction, or transfection techniques. As used herein, the terms "transduction," "transformation," and "transfection" refer to a variety of art-recognized techniques for introducing foreign nucleic acid (e.g., DNA) into a host cell, including calcium phosphate or calcium chloride co-precipitation, DEAE-dextran-mediated transfection, lipofection, electroporation, microinjection, and infection.

Expressing an Mdm2 variant in both somatic adult fibroblasts and mouse embryonic fibroblasts results in a unique system for examining the developmental and genetic effects of the variant, for example, on apoptosis, e.g., the requirements for eliciting apoptosis, or on tumorigenesis, e.g., p53-independent tumorigenesis or tumor inhibition. In mouse embryonic fibroblasts (MEFs), RNA can be isolated at various time points following infection to determine which gene messages are up- or down-regulated during the apoptotic response, thereby identifying further potential drug targets for eliciting or forestalling apoptosis or cellular proliferation. Various Mdm2 variant and/or non-Mdm2 transgenes, or other compounds, e.g., non-nucleic acid compounds such as polypeptides or small molecules can be introduced into this system and their effects assessed, e.g., to screen the genes or compounds for potential therapeutic activity. Additionally, downstream genes of p53 that are required for apoptosis to occur can be identified by comparing genes activated or downregulated in somatic versus embryonic fibroblasts, using methods known in the art, such as subtractive methods including gene chips and arrays, inter alia. Cells such as thymocytes can also be used, e.g., for examining apoptosis in response to gamma irradiation, UV, or other forms of DNA damage. Suitable thymocytes can be, for example, thymocytes harvested between 4-8 weeks post birth. Tumor cell lines may be derived from animals exhibiting tumor formation. Reactive gliosis can also be examined in astrocyte cultures, for example, astrocytes and neurons can be removed, e.g., from p0 (newborn) mice, and studied in vitro.

Methods of Screening

Also included herein are screening methods. In some embodiments, the method can be a cell culture assay including contacting cells expressing an Mdm2 variant, e.g., tumor cells derived from a transgenic animal overexpressing an Mdm2 variant, with a test compound and determining the effect of the test compound on the expression of the Mdm2 variant, or on an activity of an Mdm2 variant, e.g., on the induction of NFκB activity, e.g., using an NFκB reporter gene as described herein (see Example 4, and the Materials and Methods, below). In some embodiments, the methods include determining the effect of the test compound on proliferation of the cells. In some embodiments, the methods include determining the effect of the test compound on the expression and/or activity of a non-Mdm2 gene or polypeptide, e.g., NFκB, e.g., p65.

Transgenic animals (e.g., mice) overexpressing an Mdm2 variant, and cells derived from these animals, e.g., tumor-derived cells, can be used to screen for modulators of Mdm2 variant activity of expression. For example, the methods can include administering a test compound to a transgenic animal overexpressing an Mdm2 variant, and determining the effect of the test compound on the expression of an Mdm2 variant, or on an activity of an Mdm2 variant, and/or determining the effect of the test compound on the phenotype of the transgenic animal, e.g., the presence, absence, or severity of tumors. In some embodiments, the method includes administering the test compound to a transgenic animal that has tumors, and monitoring the animal's tumors, e.g., for tumor regression. In some embodiments, the method includes administering the test compound to a transgenic animal that has not yet developed tumors, and monitoring the animal for the development of tumors. The methods can include administration of one or more doses of the test compound.

In some embodiments, the test compound is a specific inhibitor of an Mdm2 variant as described herein, e.g., an siRNA, antisense, or antibody specific for the Mdm2 variant.

Small Molecules and Combinatorial Libraries

The methods can include high throughput screening of test compounds, e.g., small molecule test compounds, e.g., compounds that are initially members of an organic chemical library, to identify agents that specifically bind a target Mdm2 variant. A number of suitable assays known in the art can be adapted for use in high throughput screening methods. In one embodiment, an array of cells expressing an Mdm2 variant, e.g., Mdm2-b, and an NFκB reporter gene, e.g., a κB-responsive luciferase reporter plasmid containing one or more, e.g., two, canonical κB sites (5'-GGRN-NYYCC-3'), and/or a control plasmid. The array can be exposed to test compounds, and the effect of the test compound on levels of the reporter, e.g., luciferase, can be evaluated. A statistically significant decrease in expression of the reporter can be considered a positive response.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The small molecules can be natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety Libraries screened using the methods described herein can include a variety of types of small molecule test compounds. A given library can include a set of structurally related or unrelated small molecule test compounds, e.g., peptide or peptidomimetic molecules. In some embodiments, test compounds include, but are not limited to, peptide analogs including peptides comprising non-naturally occurring amino acids, e.g., β-amino acids or β-substituted β-amino acids ("β$^3$-amino acids"), phosphorous analogs of amino acids, such as α-amino phosphonic acids and α-amino phosphinic acids, or amino acids having non-peptide linkages, or other small organic molecules. In some embodiments, the small molecules are β-peptide molecules; peptidomimetics (e.g., peptoid oligomers, e.g., peptoid amide or ester analogues, β-peptides, D-peptides, L-peptides, oligourea or oligocarbamate); small peptides (e.g., tripeptides, tetrapeptides, pentapeptides, hexapeptides, heptapeptides, octapeptides, nonapeptides, decapeptides, or larger, e.g., 20-mers or more); cyclic peptides; other non-natural or unnatural peptide-like structures; and inorganic molecules (e.g., heterocyclic ring molecules). In some embodiments, the small molecules are nucleic acids.

The small molecule combinatorial libraries useful in the methods of the invention can include the types of compounds that will potentially bind to the ligand binding sites of the target Mdm2 variant used to screen them. For example, where the variant has a known protein binding partner, the test compounds can be structurally similar to the known binding partner.

In some embodiments, the small organic molecules and libraries thereof can be obtained by systematically altering the structure of a first small molecule, e.g., a first small molecule that is structurally similar to a known natural binding partner of the target Mdm2 variant, or a first small molecule identified as capable of binding the target Mdm2 variant, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

Small molecules that demonstrate a positive response (e.g., a decrease in NFκB-mediated gene expression, in methods using the NFκB reporter gene assay described herein) can be selected and systematically altered, e.g., using rational design, to optimize binding affinity, avidity, specificity, or other parameter. Such optimization can also be screened for using the methods described herein. Thus, in one embodiment, the invention includes screening a first library of small molecules using the methods described herein, identifying one or more molecules that cause a positive response in that library, subjecting those molecules to systematic structural alteration to create a second libraries of compounds structurally related to the molecule, and screening the second library using the methods described herein.

A variety of techniques useful for determining the structures of the molecule can be used in the methods described herein, e.g., NMR, Mass spectrometry, Gas chromatography equipped with Electron capture detectors, fluorescence and absorption spectroscopy. Thus, the invention also includes compounds identified by the methods described herein, and methods for their administration and use in the treatment, prevention, or delay of development or progression of a disease, e.g., cancer. One skilled in the art will also recognize that these techniques can also be used to monitor the synthesis of test compounds.

Therapeutic Compounds and Pharmaceutical Compositions

Also included herein are compounds that have been identified using the methods described herein. A test compound that has been screened by a method described herein and determined to modulate Mdm2 activity or expression, can be considered a candidate compound for the treatment of a disorder. A candidate compound that has been screened, e.g., in an in vivo model of a disorder, e.g., a cancer model, and determined to have a desirable effect on the disorder, e.g., on one or more symptoms of the disorder, can be considered a candidate therapeutic agent. Candidate therapeutic agents, once screened in a clinical setting, are therapeutic agents. Candidate therapeutic agents and therapeutic agents can be optionally optimized and/or derivatized, and formulated with physiologically acceptable excipients using known techniques to form pharmaceutical compositions. Compounds identified as reducing the expression or activity of an Mdm2 variant as described herein can be considered candidate therapeutic compounds, useful in treating disorders associated with the Mdm2 variant, e.g., cancer.

The therapeutic compounds described herein can be incorporated into pharmaceutical compositions. Such compositions typically include the nucleic acid molecule and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions. Pharmaceutical compositions are typically formulated to be compatible with their intended route of administration. Examples of routes of administration include parenteral, e.g., intravenous, intradermal, subcutaneous, oral (e.g., inhalation), transdermal (topical), transmucosal, and rectal administration.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

The pharmaceutical compositions can be included in a container, pack, or dispenser together with instructions for administration.

Detection of Mdm2 Variants

Portions or fragments of the nucleic acid sequences identified herein can be used as polynucleotide reagents. For example, these sequences can be used to diagnose a subject with a cancer associated with increased expression of an Mdm2 variant, or to form a prognosis.

The presence, level, or absence of Mdm2 variant protein or nucleic acid in a biological sample can be evaluated by obtaining a biological sample from a test subject and contacting the biological sample with a compound or an agent capable of detecting Mdm2 variant protein or nucleic acid (e.g., mRNA) that encodes an Mdm2 variant protein such that the presence of Mdm2 variant protein or nucleic acid is detected in the biological sample. The term "biological sample" includes tissues, cells, and biological fluids isolated from a subject, as well as tissues, cells, and fluids present within a subject. For example, a biological sample can be a tissue sample from a tumor, serum, or urine. The level of expression of the Mdm2 variant can be measured in a number of ways, including, but not limited to measuring the Mdm2 variant mRNA; measuring the amount of protein encoded by the Mdm2 variants; or measuring the activity of a protein encoded by the Mdm2 variants.

The level of Mdm2 variant mRNA in a cell can be determined both by in situ and in vitro formats. For example, the isolated mRNA can be used in hybridization or amplification assays that include, but are not limited to, Southern or Northern analyses, polymerase chain reaction analyses, and probe arrays. One diagnostic method for the detection of mRNA levels involves contacting the isolated mRNA with a nucleic acid molecule (probe) that can hybridize to the selected variant mRNA. The nucleic acid probe can be, for example, a full-length Mdm2 variant nucleic acid, such as the Mdm2-b nucleic acid of SEQ ID NO:11, or a portion thereof, such as an oligonucleotide of at least 15, 20, 30, 50, 100, 250 or 500 nucleotides in length, and sufficiently specific that it will specifically hybridize under stringent conditions to a preselected Mdm2 variant mRNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the presence and/or level of Mdm2 variant mRNA.

The level of mRNA in a sample given the sequences provided herein can be evaluated with nucleic acid amplification, e.g., by rtPCR (U.S. Pat. No. 4,683,202), ligase chain reaction (Barany Proc. Natl. Acad. Sci. USA 88:189-193 (1991)), self sustained sequence replication (Guatelli et al., Proc. Natl. Acad. Sci. USA 87:1874-1878 (1990)), transcriptional amplification system (Kwoh et al., Proc. Natl. Acad. Sci. USA 86:1173-1177 (1989)), Q-Beta Replicase (Lizardi et al., Bio/Technology 6:1197 (1988)), rolling circle replication (U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the Mdm2 variant being analyzed.

In another embodiment, the methods further include contacting a control sample with a compound or agent capable of detecting Mdm2 variant mRNA, and comparing the presence of Mdm2 variant mRNA in the control sample with the presence of Mdm2 variant mRNA in the test sample.

A variety of methods can be used to determine the level of protein encoded by an Mdm2 variant. In general, these methods include contacting an agent that selectively binds to the variant protein, such as an antibody with a sample, to evaluate the level of protein in the sample. In some embodiments, the antibody bears a detectable label. Antibodies can be polyclonal, but are typically monoclonal. An intact antibody, or a fragment thereof (e.g., Fab or F(ab')$_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect Mdm2 variant protein in a biological sample in vitro as well as in vivo. In vitro techniques for detection of Mdm2 variant protein include enzyme linked immunosorbent assays (ELISAs), immunoprecipitations, immunofluorescence, enzyme immunoassay (EIA), radioimmunoassay (RIA), and Western blot analysis. In vivo techniques for detection of Mdm2 variant protein include introducing into a subject a labeled anti-Mdm2 variant antibody. For example, the antibody can be labeled with a radioactive or fluorescent marker whose presence and location in a subject can be detected by standard imaging techniques.

In another embodiment, the methods further include contacting the control sample with a compound or agent capable of detecting Mdm2 variant protein, and comparing the presence of Mdm2 variant protein in the control sample with the presence of Mdm2 variant protein in the test sample.

The invention also includes kits for detecting the presence of Mdm2 variant in a biological sample. For example, the kit can include a compound or agent capable of detecting Mdm2 variant protein or mRNA in a biological sample; and a standard. The compound or agent can be packaged in a suitable container. The kit can further include instructions for using the kit to detect Mdm2 variant protein or nucleic acid.

For antibody-based kits, the kit can include: (1) a first antibody (e.g., attached to a solid support) that binds to a polypeptide corresponding to a marker described herein; and, optionally, (2) a second, different antibody that binds to either the polypeptide or the first antibody and is conjugated to a detectable agent.

For oligonucleotide-based kits, the kit can include: (1) an oligonucleotide, e.g., a detectably labeled oligonucleotide, that hybridizes to a nucleic acid sequence encoding a polypeptide corresponding to a marker described herein or (2) a pair of primers useful for amplifying a nucleic acid molecule corresponding to a marker described herein. The kit can also includes a buffering agent, a preservative, or a protein stabilizing agent. The kit can also includes components necessary for detecting the detectable agent (e.g., an enzyme or a substrate). The kit can also contain a control sample or a series of control samples that can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with mis-expressed or aberrant or unwanted Mdm2 variant expression or activity, e.g., overexpression.

In one embodiment, a disease or disorder associated with aberrant Hdm2 variant expression or activity is identified. A test sample is obtained from a subject, and Hdm2 variant protein or nucleic acid (e.g., mRNA) is evaluated, wherein the level, e.g., the presence or absence, of Hdm2 variant protein or nucleic acid is diagnostic for a subject having or at risk of developing a disease or disorder associated with aberrant, e.g., excessive, Hdm2 variant expression or activity. A preferred Hdm2 variant is Hdm2-b.

The assays described herein can be used to determine whether a subject can or should be administered an agent (e.g., an agonist, antagonist, peptidomimetic, protein, peptide, nucleic acid, small molecule, or other drug candidate) to treat a disease or disorder associated with aberrant Hdm2 variant expression or activity. For example, such methods can be used to determine whether a subject can be effectively treated with an agent for a cancer associated with expression of an Hdm2-b variant.

In some embodiments, the methods include evaluating NFκB levels or activity in a sample from a subject, such as a sample including cells or tissue from a tumor biopsy. The presence of an elevated NFκB level or activity indicates that the subject is a candidate for treatment with an inhibitor of an Hdm2 variant, e.g., an Hdm2-b inhibitor. NFκB activity can be measured using methods known in the art, e.g., using an NFκB reporter assay as described herein, e.g., in a cell extract. NFκB levels can be measured using methods known in the art, e.g., immunologically-based protein detection methods, or methods that detect levels of nucleic acids.

The new methods can also be used to detect expression of an Hdm2 and/or Mdm2 variant, thereby determining if the subject is at risk for a disorder characterized by misregulation in an Mdm2 variant protein activity or expression, such as a cancer. In some embodiments, the methods include detecting, in a sample from the subject, the presence or absence of an Mdm2 variant transcript or polypeptide. This method can include the steps of collecting a sample of cells from a subject, isolating nucleic acid (e.g., mRNA) from the sample, contacting the nucleic acid sample with one or more primers that specifically hybridize to an Mdm2 variant mRNA under conditions such that hybridization and amplification of the Mdm2 variant mRNA (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, expression of an Mdm2 variant in a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates expression of a variant cDNA. Moreover, the use of sequence specific ribozymes (see, for example, U.S. Pat. No. 5,498,531) can be used to detect and score for the presence of specific variant sequences (e.g., splice site sequences) by development or loss of a ribozyme cleavage site.

In other embodiments, alterations in electrophoretic mobility will be used to identify expression of Mdm2 variants.

The methods described herein can be performed, for example, by utilizing pre-packaged diagnostic kits comprising at least one probe nucleic acid or antibody reagent described herein, which can be conveniently used, e.g., in clinical settings to diagnose patients exhibiting symptoms, e.g., tumors, e.g., p53-deficient tumors, or family history of a disease or illness involving an Mdm2 variant.

In some embodiments, the methods include determining the level of NFκB expression or activity. A number of methods are known in the art for doing so, e.g., the protein and nucleic acid detection methods described herein. The methods can including detecting the presence and/or level of one or more of the subunit proteins of NFκB, e.g., p50 (Murine: GenBank Accession No. NP_032715, UniProt accession number P25799, described in Ghosh et al., Cell 62(5):1019-29 (1002); Homo Sapiens: GenBank Accession No. NP_003989, AAA36408, described in Meyer et al., Proc Natl Acad Sci USA. 88(3):966-70 (1991)) and/or p65 (Murine: UniProt accession numbers Q04207, Q62025, described in Linker et al., Gene 176:119-124 (1996); Homo Sapiens: GenBank Accession No. A40851, UniProt accession number Q04206, described in Ruben et al., Science 251, 1490-1493 (1991)). Antibodies to the subunits are available commercially, e.g., from Research Diagnostics Inc., Flanders, N.J.; Imgenex Corp., Sorrento Valley, Calif.; and others. A number of assays of NFκB activity are known in the art, and include the NFκB reporter assay described herein.

Specific Inhibitors of Mdm2 Variants

The invention also includes specific inhibitors of Mdm2 variants, e.g., compounds that inhibit the expression or activity of an Mdm2 variant, while leaving the expression or activity of the full-length Mdm2 untouched. Such specific inhibitors can include antibodies, antisense nucleic acids, ribozymes, or siRNAs that are specific for sequences present in the variants but absent in the full-length transcripts. For example, nucleic acids that include unique nucleotide sequences spanning a splice junction, can be used to achieve specific disruption of expression, and not interfere with full length mdm2. Peptides including unique amino acid sequences spanning a splice junction can be used, e.g., to generate antibodies specific for the splice variants.

RNA Interference

RNAi is a remarkably efficient process whereby double-stranded RNA (dsRNA, also referred to herein as si RNAs or ds siRNAs, for double-stranded small interfering RNAs,) induces the sequence-specific degradation of homologous mRNA in animals and plant cells (Hutvagner and Zamore, Curr. Opin. Genet. Dev.: 12, 225-232 (2002); Sharp, Genes Dev., 15:485-490 (2001)). In mammalian cells, RNAi can be triggered by 21-nucleotide (nt) duplexes of small interfering RNA (siRNA) (Chiu et al., Mol. Cell. 10:549-561 (2002); Elbashir et al., Nature 411:494-498 (2001)), or by micro-RNAs (miRNA), functional small-hairpin RNA (shRNA), or other dsRNAs that are expressed in vivo using DNA templates with RNA polymerase III promoters (Zeng et al., Mol. Cell 9:1327-1333 (2002); Paddison et al., Genes Dev. 16:948-958 (2002); Lee et al., Nature Biotechnol. 20:500-505 (2002); Paul et al., Nature Biotechnol. 20:505-508 (2002); Tuschl, Nature Biotechnol. 20:440-448 (2002); Yu et al., Proc. Natl. Acad. Sci. USA 99(9):6047-6052 (2002); McManus et al., RNA 8:842-850 (2002); Sui et al., Proc. Natl. Acad. Sci. USA 99(6):5515-5520 (2002).)

Accordingly, the invention includes such molecules that are targeted to an Mdm2 variant RNA. In some embodiments, the siRNA spans the splice site of Mdm2-b, e.g., the sequence immediately surrounding G104-G105 of SEQ ID NO:11. In some embodiments, the siRNA comprises all or part of the sequence:

```
GGAACAAGAGACTCTGGACTATTGG.    (SEQ ID NO:15)
``` siRNA Molecules

The invention includes dsRNA molecules comprising 16-30 nucleotides, e.g., 16, 17, 18, 19, 20, 21, 22, 23, 24, 25, 26, 27, 28, 29, or 30 nucleotides, in each strand, wherein one of the strands is substantially identical, e.g., at least 80% or more, (e.g., 85%, 90%, 95%, or 100%) identical, e.g., having 3, 2, 1, or 0 mismatched nucleotide(s), to a target region in the Mdm2 variant mRNA, and the other strand is identical or substantially identical to the first strand. The dsRNA molecules described herein can be chemically synthesized, or can be transcribed in vitro from a DNA template, or in vivo from, e.g., shRNA. The dsRNA molecules can be designed using any method or algorithm known in the art, and will typically be designed to target a unique sequence in the Mdm2 variant, e.g., a sequence spanning the variant splice junction.

Negative control siRNAs should have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

The nucleic acid compositions include crosslinked nucleic acid derivatives. Crosslinking can be employed to alter the pharmacokinetics of the composition, for example, to increase half-life in the body. Thus, the invention includes siRNA derivatives that include siRNA having two complementary strands of nucleic acid, such that the two strands are crosslinked. For example, a 3' OH terminus of one of the strands can be modified, or the two strands can be crosslinked and modified at the 3'OH terminus. The siRNA derivative can contain a single crosslink (e.g., a psoralen crosslink). In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The nucleic acid compositions described herein can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The nucleic acid molecules described herein can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3$H, $^{32}$P, or other appropriate isotope.

The dsRNA molecules can comprise the following sequences as one of their strands, and allelic variants thereof:

siRNA Delivery for Longer-term Expression

Synthetic siRNAs can be delivered into cells by cationic liposome transfection and electroporation. However, these exogenous siRNA only show short term persistence of the silencing effect (4~5 days). Several strategies for expressing siRNA duplexes within cells from recombinant DNA constructs allow longer-term target gene suppression in cells, including mammalian Pol III promoter systems (e.g., H1 or U6/snRNA promoter systems (Tuschl (2002), supra) capable of expressing functional double-stranded siRNAs; (Bagella et al., J. Cell. Physiol. 177:206-213 (1998); Lee et al. (2002), supra; Miyagishi et al. (2002), supra; Paul et al. (2002), supra; Yu et al. (2002), supra; Sui et al. (2002), supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into the cells with a vector expression T7 RNA polymerase (Jacque (2002), supra).

Animal cells express a range of noncoding RNAs of approximately 22 nucleotides termed micro RNA (miRNAs) and can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with miRNA sequence complementary to the target mRNA, a vector construct that expresses the novel miRNA can be used to produce siRNAs to initiate RNAi against specific mRNA targets in mammalian cells (Zeng (2002), supra). When expressed by DNA vectors containing polymerase III promoters, micro-RNA designed hairpins can silence gene expression (McManus (2002), supra). Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., Proc. Natl. Acad. Sci. USA 99(22):14236-40 (2002)). In adult mice, efficient delivery of siRNA can be accomplished by "high-pressure" delivery technique, a rapid injection (within 5 seconds) of a large volume of siRNA containing solution into animal via the tail vein (Liu (1999), supra; McCaffrey (2002), supra; Lewis, Nature Genetics 32:107-108 (2002)). Nanoparticles and liposomes can also be used to deliver siRNA into animals.

Antisense

An "antisense" nucleic acid can include a nucleotide sequence that is complementary to a "sense" nucleic acid encoding a protein, e.g., complementary to the coding strand of a double-stranded cDNA molecule or complementary to an Mdm2 variant mRNA sequence. An antisense nucleic acid can be designed such that it is complementary to the entire coding region of a target Mdm2 variant mRNA, e.g., Mdm2-b mRNA, but can also be an oligonucleotide that is antisense to only a portion of the coding or noncoding region of the target mRNA, should include a sequence unique to the variant, e.g., a sequence spanning a splice junction. For example, the antisense oligonucleotide can be complementary to the region surrounding the splice site of the variant mRNA, e.g., between the −10 and +10 regions of the splice site of the variant. An antisense oligonucleotide can be, for example, about 10, 15, 20, 25, 30, 35, 40, 45, 50, 55, 60, 65, 70, 75, 80, or more nucleotides in length.

Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides spanning the length of a Mdm2 or Hdm2 variant nucleic acid can be prepared, followed by testing for inhibition of Mdm2/Hdm2 variant expression. Optionally, gaps of 5-10 nucleotides can be left between the oligonucleotides to reduce the number of oligonucleotides synthesized and tested.

The new antisense nucleic acids can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acids also can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules described herein are typically administered to a subject (e.g., by direct injection at a tissue site), or generated in situ such that they hybridize with or bind to cellular mRNA encoding an Mdm2 variant protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. For example, to achieve sufficient intracellular concentrations of the antisense molecules, vector constructs in which the antisense nucleic acid molecule can be placed under the control of a strong pol II or pol III promoter can be used.

In yet another embodiment, the new antisense nucleic acid molecules can be α-anomeric nucleic acid molecules. An α-anomeric nucleic acid molecule forms specific double-stranded hybrids with complementary RNA in which, contrary to the usual β-units, the strands run parallel to each other (Gaultier et al., Nucleic Acids. Res. 15:6625-6641 (1987)). The antisense nucleic acid molecule can also comprise a 2'-o-methylribonucleotide (Inoue et al. Nucleic Acids Res. 15:6131-6148 (1987)) or a chimeric RNA-DNA analogue (Inoue et al. FEBS Lett., 215:327-330 (1987)).

Ribozymes

A ribozyme is a type of RNA that is engineered to enzymatically cleave and inactivate another RNA target in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for an Mdm2 variant-encoding nucleic acid can include one or more sequences complementary to the nucleotide sequence spanning a splice junction of an Mdm2 variant cDNA disclosed herein, and a sequence having known catalytic sequence responsible for mRNA cleavage (see U.S. Pat. No. 5,093,246 or Haselhoff and Gerlach, Nature 334:585-591 (1988)). For example, a derivative of a Tetrahymena L-19 IVS RNA can be constructed in which the nucleotide sequence of the active site is complementary to the nucleotide sequence to be cleaved in a sequence spanning a splice junction of an Mdm2 variant-encoding mRNA. See, e.g., Cech et al. U.S. Pat. No. 4,987,071; and Cech et al., U.S. Pat. No. 5,116,742. Alternatively, RNA including a sequence spanning a splice junction of an Mdm2 variant can be used to select a catalytic RNA having a specific ribonuclease activity from a pool of RNA molecules. See, e.g., Bartel and Szostak, Science 261:1411-1418 (1993).

EXAMPLES

The invention is further described in the following examples, which do not limit the scope of the invention described in the claims.

Materials and Methods:

Isolation of Alternatively-Spliced Mdm2 Transcripts: Total RNA was isolated from dounce homogenized, snap-frozen transgenic mouse tumor tissue using TRIzol® (Invitrogen). RT-PCR was performed using Superscript™ First-Strand Synthesis System (Invitrogen). RNA was reverse transcribed using an oligo (dT) primer. The resulting cDNA was used in nested PCR utilizing primer pair Ex2forward (5'-CTGCTGGGCGAGCGGGAGACC-3'; SEQ ID NO:1) and Ex12reverse (5'-GTGGACTAAGA-CAGTTTTCTGGC-3'; SEQ ID NO:2) for the first amplification of 25 cycles followed by a second amplification with primer pair Ex2nest (5'-GACCCTCTCGGATCACCGCGC-3'; SEQ ID NO:3) and Ex12nest (5'-GTGAGCAGGT-CAGCTAGTTGA-3'; SEQ ID NO:4) for a total of 35 cycles of 94° C. for 2 minutes, 94° C. for 30 seconds, 55° C. for 30 seconds, and 72° C. for 60 seconds. PCR products were resolved on 1% agarose gels, excised, purified (using GENECLEAN™), and cloned into pGEM®-T Easy Vector (Promega) for sequencing. PCR identification of specific Mdm2-b isoform was done using primer pair MBforward (5'-AAGAGACTCTGGACTATTGGAAGTG-3'; SEQ ID NO:5) and 12reverse (5'- GCAGATCACACATGGTTC-GATGGCA-3'; SEQ ID NO:6). DNA sequencing of cDNAs was performed by the University of Massachusetts Nucleic Acid Facility to identify Mdm2-specific isoforms.

Cloning and Expression of the Mdm2-b Isoform: Mdm2-b and Hdm2-b cDNAs were cloned into the EcoRI sites of pBabe-PURO and pcDNA3.1HisC expression plasmids (Invitrogen). Mdm2-B$^{ssp1}$ was generated using primer pair 176F (5'-CCTAAAAATGGCAATATTGTTCACG-GCAAGAC -3'; SEQ ID NO:7) and 176R (5'-GTCTTGC-CGTGAACAATATTGCCATTTTTAGG-3'; SEQ ID NO:8) with the QUIKCHANGE® Site-Directed Mutagenesis kit (Stratagene). The presence of the C176N mutation was confirmed by an SspI restriction enzyme digestion and by DNA sequencing. Mdm2-b and Mdm2-b$^{ssp1}$ protein products were confirmed using an in vitro transcription and translation system in rabbit reticulocyte lysates (Promega).

Cell Culture, Cell Lines, and Antibodies: NIH3T3 cells were purchased from the ATCC. Mouse Embryonic Fibroblasts (MEFs) null for pRB or p53 were generated using standard protocols. p19(ARF)-null MEFs were kindly provided by the Kowalik lab at UMASS Medical School. All cells were maintained in DMEM supplemented with 10% FCS, (100 U/ml) of penicillin and (100 µg/ml) of streptomycin. Stable cell lines were passaged in media containing (3 µg/ml) puromycin (Sigma). Stable transfection of NIH3T3 cells were performed in 100 mm plates using 10 µg of linearized expression plasmid DNA along with FuGene reagent (Roche), according to manufacturer's protocol. Following puromycin drug selection, surviving colonies were pooled for the generation of stable cell lines. For immunolocalization studies, $2\times10^5$ cells were seeded onto coverslips in the bottom of six-well plates. Transient transfections were performed using 1 µg of Express-Mdm2-b, Express-AML3, or Express-empty vector using Lipofectamine™ (Invitrogen). Foci formation was scored in NIH3T3 stable cell lines following methanol fixation and 0.1% crystal violet after 2 weeks of culture.

Bosc293 cells at 80% confluency were transfected with 10 µgs of pBabe-Mdm2-b, pBabe-Mdm2-b$^{ssp1}$, pBabe-Hdm2-b, or pBabe control using Lipofectamine™ to generate recombinant retrovirus. Forty-eight hours following transfection, retroviral particles were collected and used for the viral transduction of primary MEFs or NIH3T3 cells seeded at $1\times10^6$ cells per 100 mm plate.

Monoclonal antibodies against the C-terminus of Mdm2 (C-18) and polyclonal anti-p65 antibody (C-20) were purchased from Santa Cruz Biotechnology, Inc. Primary polyclonal antibody Ab-7 (Oncogene Research Products) was used to detect p53, followed by secondary biotin-conjugated rabbit anti-sheep IgG (Oncogene Research Products), and tertiary HRP-conjugated streptavidin (Zymed Laboratories Inc.) Anti-Xpress™-FITC antibody (Invitrogen) was used for immunolocalization studies. An anti-BrdU antibody (Becton Dickinson) was used to label cells for FACS analysis. Anti-Tubulin monoclonal antibody (Sigma) was used for protein loading control.

Analysis of Cell Proliferation: Growth curves were performed with triplicate plating of either NIH3T3 stable cell lines, p53-/-, p19-/-, or pRB-/- Puro$^R$ early passage MEFs. Cells w seeded at a density of $2\times10^5$ cells per 60 mm plate and counted every 24 hours using a Beckman Coulter Counter. For the determination of asynchronous S phase populations, cells were seeded at $1\times10^6$ cells per 100 mm plate and pulsed 24 hours later with 10 µm BrdU for 1 hour. FACS analysis was performed on cells stained for BrdU and propidium iodide using standard methodology by the UMASS Medical School FACS Facility.

Analysis of Cell Death: NIH3T3 cell lines were 50-60% confluent when treated with (500 ng/ml) doxorubicin (Sigma). Triplicate samples of cells were harvested 24-36 hours later and analyzed for propidium iodide uptake by FACS Analysis.

NFκB Activity Assays: 293T cells were seeded into six-well plates at a density of $5 \times 10^5$ cells in 2 mls of medium and transfected with 50 ng of each of an internal β-galactosidase transfection efficiency control plasmid and either a κB-responsive luciferase reporter plasmid containing two canonical κB sites or a control plasmid lacking κB sites together with Mdm2-b, Mdm2-b$^{ssp1}$, or control pcDNA3.1 expression plasmids. Cells were treated with recombinant TNF-α (Boehringer Mannheim) and 24 to 36 hours following transfection, luciferase assays (Promega) were performed using a luminometer as previously described (Duckett et al., Mol. Cell. Biol. 17:1535-1542 (1997)).

Immunolocalization Assays: Forty-eight hours following transient transfection, cells on coverslips were fixed with (3.7%) formaldehyde in PBS, permeabilized with (0.25%) Triton® X-100 in PBS, and blocked in (0.5%) BSA in PBS prior to a one-hour incubation with an Anti-Xpress™-FITC conjugated antibody for the recognition of Mdm2-b or AML3. Cell nuclei were stained with DAPI (0.5 µg DAPI in 0.1% Triton® X-100-PBSA). Cells were visualized using a Zeiss Confocal Microscope.

Generation of Transgenic Mice: Mdm2-b cDNA was cloned into the EcoRI sites of transgene cassettes pCAGGs (a gift from Paul Overbeek at Baylor College of Medicine, and GFAP (a gift from Michael Brenner). Transgenic mice were generated via pronuclear injection using standard procedures. Identification of GFAP-Mdm2-b founder mice and transmission of the transgene was determined by PCR and Southern Analyses. The PCR primers used for genotyping span the junction of cDNA to MP-1pA, TGforward 5'-CCAATCCAAATGATTGTGCTA-3' (SEQ ID NO:9) and TGreverse 5'-CATTGTTCCTTAGCAGGCTCC-3' (SEQ ID NO:10). Southern analysis was performed on EcoRI digested genomic tail DNA using Mdm2-b cDNA as a probe, and densitometry using a PhosphorImager™ identified the relative copy number of transgenes in each line. Research involving mice complied with all relevant federal and institutional policies, as well as guidelines established by the Institutional Animal Care and Use Committee (IACUC) at UMASS Medical School.

Example 1

Isolation and Characterization of Mdm2-b

To determine whether Mdm2 splice variant transcripts are present in Mdm2-transgenic mouse tumors, RNA was extracted from 14 frozen tumor samples, and RT-PCR was performed using nested PCR amplification. PCR products were analyzed by gel electrophoresis (FIG. 1A), and Southern hybridization using various Mdm2 oligonucleotide probes spanning the Mdm2 coding sequences. The majority of splice variants hybridized to 3' probes corresponding to exon 12 of the Mdm2 gene. To isolate individual splice variants, nested Mdm2 PCR products were purified and 72 transcripts were subcloned into plasmid vectors. Subsequent DNA sequencing of the cDNA clones revealed a wide variety of Mdm2 splice variants and included both aberrant transcripts resulting from cryptic splice sites within introns and exons as well as transcripts generated from the donor and acceptor splice sites located at the Mdm2 intron-exon boundaries (Jones et al., Gene, 175:209-213 (1996)). The most prevalent transcript observed was a homologue of Hdm2-B, the most frequently detected Hdm2 splice variant found in human tumors (Sigalas et al., Nat. Med. 2:912-917 (1996); Bartel et al., Cancer Cell 2:9-15 (2002)). This mouse Mdm2-b isoform was detected in all 14 analyzed tumor samples, and was not detected in wildtype tissue in these experiments (FIG. 1B).

The Mdm2-b transcript (SEQ ID NO:11) encodes sequences present in Mdm2 exons 1-3 and exon 12, with RNA splicing between exons 3 and 12 occurring at the precise exon splice donor-acceptor motifs (triangles, FIG. 1C). The predicted protein alignment between Mdm2-b (SEQ ID NO:12) and Hdm2-b (SEQ ID NO:14) is illustrated (FIG. 1C). Amino acid identity between the two proteins is about 82-84%. The encoded Mdm2-b protein lacks the p53-binding, p300-binding, pRb-binding, and p19(ARF) binding domains present on full length Mdm2, as well as the Mdm2 nuclear localization and nuclear export signals. Mdm2-b contains the complete C-terminal zinc finger, RING finger domain, and Mdm2 residues that have been identified as targets for phosphorylation by ATM (Maya et al., Genes Dev. 15:1067-1077 (2001), de Toledo et al., Oncogene 19:6185-93 (2000)) and c-Ab1 (Sionov et al., J. Biol. Chem. 274:8371-8374 (1999)).

To confirm that the Mdm2-b spliced transcript encodes for a protein product, Mdm2-b cDNA was cloned into pcDNA3.1 in frame with an N-terminal Xpress™ epitope tag (Invitrogen) and expressed the protein in an in vitro transcription/translation expression system (Promega). In addition, a single cysteine residue in the RING domain of Mdm2-b (Mdm2-b$^{ssp}$) was mutated for use in subsequent studies. The Mdm2-b transcript encodes a protein product of approximately 47 kD in size, when the size of the 3.5 kD Xpress tag is subtracted (FIG. 1D). To determine the cellular location of the Mdm2-b protein, the pcDNA-Xpress™ Mdm2-b vector was transiently transfected into NIH3T3 cells and immunofluorescence microscopy was performed using an α-XPRESS™-FITC-conjugated antibody against XPRESS™-Mdm2-b. Mdm2-b was determined to localize predominantly in the cytoplasm of the transfected NIH3T3 cells (FIG. 1E), in keeping with the absence of a nuclear localization signal on Mdm2-b. An XPRESS™ tagged-AML3 expression plasmid that encodes a protein that localizes to the nucleus was used in parallel as a control in this experiment. The results of this experiment indicate that the Mdm2-b variant is expressed as a protein product.

Example 2

Expression of Mdm2-b Increases Cell Proliferation and Transformation

Numerous spliced forms of Mdm2, including the B isoform, have been identified previously in human tumors (Sigalas et al., (1996), supra; Dang et al., (2002), supra; Evans et al., (2001), supra). However, there have been contradictory reports as to the effect of the splice forms upon cell growth (Id.). Therefore, the contribution of the presence of the Mdm2-b isoform to the malignant phenotype of our Mdm2-transgenic mice was examined. Hdm2-b and Mdm2-b cDNAs were cloned separately into the pBabe retroviral expression vector and stably transduced into NIH3T3 cells to examine if Hdm2-b or Mdm2-b is capable of altering cellular growth characteristics. Selection for puromycin resistant clones indicated a transduction frequency of approximately 90%. Following drug selection, the stable transfectants were pooled and the expression of spliced variants was confirmed with RT-PCR and Northern blotting.

Cell proliferation assays were performed using triplicate plates of NIH3T3 cells transduced with Hdm2-b, Mdm2-b, or empty vector (pBABE) (FIG. 2A). Repeat experiments revealed that the presence of either Hdm2-b or Mdm2-b increased the proliferation rate of NIH3T3 cells, and cells bearing Mdm2-b grew to a higher saturation density than did the control transduced cells.

To investigate the role of the RING finger domain of Mdm2-b in altering cell proliferation, an Mdm2-b point mutant (Mdm2-b$^{ssp1}$) was generated that replaces a cysteine residue at Mdm2-b amino acid position 176 with an arginine residue. This mutation corresponds to the C449S mutation that renders Mdm2 incapable of ubiquitinating p53 in vivo (Fang et al., (2000), supra). This amino acid substitution did not alter the stability of the Mdm2-b protein, but should interfere with formation of the zinc RING finger. Transduction of Mdm2-b$^{ssp1}$ was performed in parallel with Mdm2-b and control (pBABE-empty vector) into NIH3T3 cells. BrdU staining of asynchronous growing cells transduced with Mdm2-b revealed a 21% increase in the numbers of cells present in S phase of the cell cycle relative to control transduced cells, whereas Mdm2-b$^{ssp1}$ transduction increased cell growth to a lesser extent (FIG. 2B). Thus, the RING domain is important to the pro-proliferative effects of Mdm2-b.

Transduction of Mdm2-b into NIH3T3 cells was found to promote obvious rapid cell proliferation. BrdU staining of asynchronous growing cells transduced with Mdm2-b or with control (pBABE-empty vector) revealed an increase in the numbers of Mdm2-b transduced cells present in S phase of the cell cycle relative to control transduced cells (FIG. 2A). To confirm the positive effects of the B splice form on cell growth, cell proliferation assays were performed using triplicate plates of NIH3T3 cells transduced with Hdm2-B, Mdm2-b, or empty vector (pBABE) (FIG. 2B). Three repeat experiments confirmed that the presence of either Hdm2-B or Mdm2-b increased the proliferation rate and saturation density of NIH3T3 cells.

To determine whether Mdm2-b could contribute to cellular transformation, Mdm2-b-expressing NIH3T3 cells and control pBabe NIH3T3 cells were seeded onto 60 mm dishes and maintained in culture for two weeks. Following crystal violet staining, foci formation was scored from six representative plates of each cell line (FIG. 2C). Mdm2-b expression induced larger and more numerous foci in the monolayer (44.6±4.5 foci per plate) than did transduction with pBabe alone (18.2±5.7 foci per plate). Thus, expression of Mdm2-b in NIH3T3 cells accelerates the rate of cell proliferation and interferes with growth suppression induced by contact inhibition.

Example 3

Mdm2-b Increases Cell Proliferation Independent of p53, p19(ARF), and Rb

Unlike full-length Mdm2, Mdm2-b lacks the p53-binding domain of Mdm2. To determine if Mdm2-b functions through p53 to increase cell proliferation, recombinant Mdm2-b retroviruses were used to transduce early passage, primary mouse embryonic fibroblasts (MEFs) derived from p53-null mice. Transient selection of the MEFs in puromycin indicated a 95% transduction frequency. The pooled MEFs were triplicate plated in 60 mm dishes and growth rates were monitored for each cell type over a period of 5 days in culture. Results of the growth curves clearly demonstrate the ability of both Hdm2-b and Mdm2-b to increase the rate of cellular proliferation when p53 is absent (FIG. 2c). Similar to the results obtained in the NIH3T3 cells, retroviral-mediated transduction of the Mdm2-b$^{ssp1}$ mutant form was less capable of enhancing the rate of p53-null MEF cell proliferation (FIG. 2d).

In addition to the p53-binding region, Mdm2-b also lacks both p19ARF and pRb binding domains. To determine the proliferative effect this splice variant has on cells lacking either p19ARF or pRb, early passage p19ARF-null MEFs or Rb-null MEFs were infected with Hdm2-b or pBabe-control retrovirus, pooled those cells surviving drug selection, and used resulting cells for proliferation curves. Similar to results obtained with p53-null cells, Hdm2-b accelerates growth in the absence of either p19(ARF) or pRb (FIG. 2e). These data indicate that the b form does not depend upon the presence of p53, p19, or Rb to increase the rate of cell growth.

Example 4

Expression of Mdm2-b Interferes with Apoptosis

Apoptosis is an important cellular mechanism for preventing transformation and neoplastic growth, and Mdm2-b mediated inhibition of apoptosis could also contribute to tumorigenesis. To determine if the Mdm2-b form alters the apoptotic response of cells, three separate, pooled 3T3 cell lines transduced with either Mdm2-b or control empty vector (pBABE) were exposed to the topoisomerase inhibitor, doxorubicin. Doxorubicin is an anthracycline analogue previously reported to induce p53-dependent and independent apoptosis. Cells were approximately 50-60% confluent when doxorubicin was added to cell culture media (500 ng/ml final concentration). Thirty-six hours following treatment, propidium iodide staining and FACS analysis of the cells revealed that 37% of control-transduced, 3T3 cells were undergoing apoptosis in comparison to 15% of Mdm2-b transduced, 3T3 cell lines (FIG. 3a). When the mutant Mdm2-b$^{ssp1}$ was transduced in parallel in the doxorubicin experiments, no inhibition of apoptosis was observed (FIG. 3a). Thus, the RING finger of Mdm2-b plays a critical role in inhibiting apoptosis of cells in response to doxorubicin.

Although p53 protein levels are elevated in the control-transduced cells, Mdm2-b transduced cells, and in the Hdm2-B -transduced cells 18 hours after doxorubicin treatment, no reduction was observed in p53 protein levels in cells transduced with the b isoforms relative to the control cells, indicating that Mdm2-b or Hdm2-B does not alter p53 levels in these cells (FIG. 3A). Furthermore, the presence of Mdm2-b in 3T3 cells does not inhibit p53-mediated induction of genes such as p21 (Waf/Cip) following treatment with 8 Gy ionizing radiation (IR) and Mdm2-b transduced cells undergo a G1 arrest in response to IR (data not shown). Furthermore, the presence of Mdm2-b in 3T3 cells does not inhibit p53-mediated induction of genes such as p21 (Waf/Cip) following treatment with 8 Gy ionizing radiation (IR) and Mdm2-b transduced cells undergo a G1 arrest in response to IR (data not shown). These data suggest that the Mdm2-b splice variant does not alter p53 stability or activity.

Another potent regulator of apoptosis in cells is the NFκB transcription factor, a dimeric complex composed of the transcriptionally inactive p50 subunit and the p65 (RelA) subunit, which contains a potent transactivation domain (Schmitz and Baeuerle, EMBO J. 10:3805-3817 (1991)). The activity of NFκB is suppressed by interaction with IkB proteins that sequester NFκB in the cytoplasm (Malek et al., J. Biol. Chem. 273:25427-25435 (1998)). NFκB suppresses apoptosis induced by tumor necrosis factor (TNF), by doxorubicin, and by other apoptotic stimuli by inducing the expression of several anti-apoptotic genes, including Bcl-xL, cIAP1 and 2, TRAF 1 and 2, and A1/Bfl2 (Glasgow et al., J. Neurochem. 75:1377-1389 (2000) Wang et al., Science 281:1680-1683 (1998); Wang et al., Mol. Cell. Biol. 19:5923-5929 (1999)), and NFκB has been implicated in upregulation of other cell cycle regulatory genes with potential oncogenic functions (Karin et al., supra). Furthermore, full-length Mdm2 has been reported to bind to sp1 sites present in the promoter region of RelA and to induce transcription of the RelA gene.

Figure 3B:
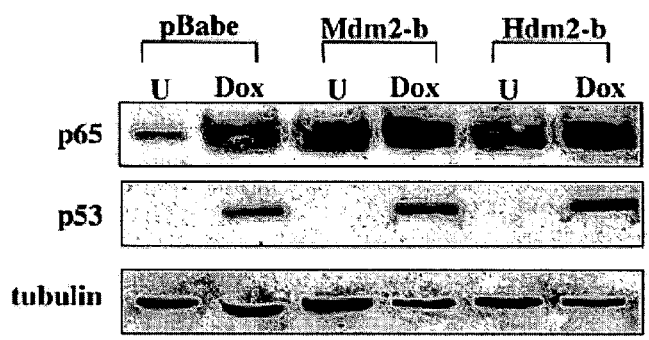
FIG. 3B is a representation of a Western blot of untreated cells (U) or cells treated with doxorubicin for 18 hrs (Dox).

Although the Mdm2-b form lacks the putative acidic activation domain of full-length Mdm2 and is unlikely to directly induce expression of heterologous genes such as RelA, the anti-apoptotic effects of RelA in doxorubicin-treated cells led to the examination of Rel A levels in the transduced cells. RelA was strongly elevated in the control-transduced 3T3 cells following doxorubicin treatment of the cells (FIG. 3A). The presence of Mdm2-b or Hdm2-b correlated with a large increase in the level of RelA in the transduced cells in the absence of any treatment, and a further increase in the amount of RelA in transduced cells treated with doxorubicin (FIG. 3B). Furthermore, both Mdm2-b and full-length Mdm2 upregulated RelA protein levels in transduced p53-deficient MEFs. However, northern analysis and real-time PCR of p65 message levels in 3T3 cells mock-transduced or transduced with Mdm2-b indicated that upregulation of p65 by Mdm2-b does not occur at the level of transcription or message stability. Interestingly, the presence of the B form correlates with a decrease in IκBα protein levels (FIG. 3B), suggesting that Mdm2-b might induce NFκB activity by interfering with the negative regulator of p65, which, in turn, leads to increased levels of p65 in the cell.

Figure 3C:
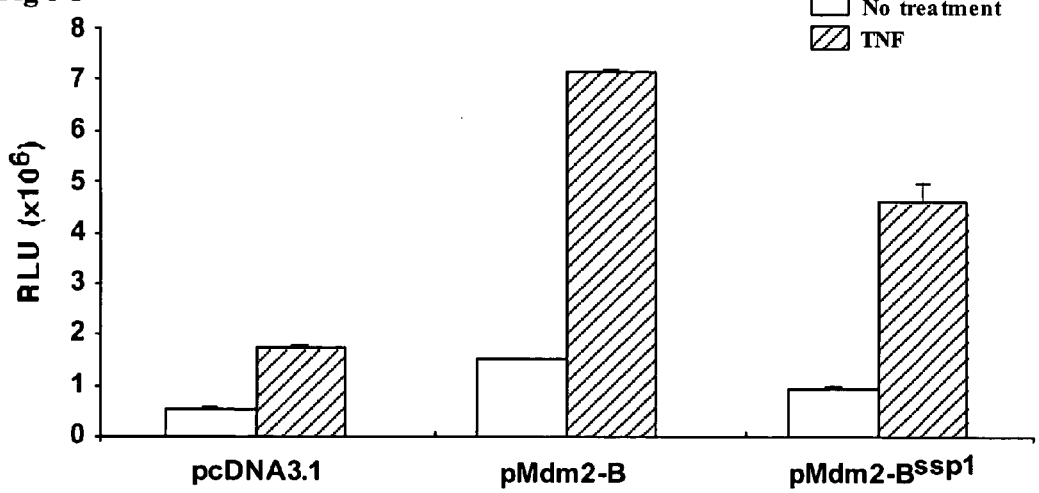
FIG. 3C is a bar graph of NFκB response to TNF-alpha treatment in 293T cells transiently transfected with Mdm2-b, Mdm2-b$^{Ssp1}$, or pCDNA3.1 (control).

To determine if induction of p65 by the Mdm2-b form alters the apoptotic response of cells, three separate, pooled 3T3 cell lines transduced with either Mdm2-b or control empty vector (pBABE) were treated with doxorubicin and the apoptotic response of the cells was compared. Cells were approximately 50-60% confluent when doxorubicin was added to cell culture media (500 ng/ml final concentration). Thirty-six hours following treatment, propidium iodide staining and FACS analysis of the cells revealed that 37% of control-transduced, 3T3 cells were undergoing apoptosis in comparison to 15% of Mdm2-b transduced, 3T3 cell lines (FIG. 3C).

To confirm that apoptosis was altered by transduction of Mdm2-b and to explore the anti-apoptotic role of the RING finger domain of Mdm2-b, an Mdm2-b point mutant (Mdm2-b$^{ssp1}$) was generated that replaces a cysteine residue at Mdm2-b amino acid position 176 with an arginine residue. This amino acid has been previously mutated in Mdm2 (C449S), and alteration of this residue interfere with formation of the zinc RING finger and compromises the ability of full-length Mdm2 to function as a ubiquitin ligase in vivo (45). This amino acid substitution did not alter the stability of the Mdm2-b protein. However, when mutant Mdm2-b$^{ssp1}$ transduction was performed in parallel in the doxorubicin experiments, no inhibition of apoptosis was observed (FIG. 3C), indicating that the RING finger of Mdm2-b is important in Mdm2-b mediated inhibition of apoptosis.

To confirm that the Mdm2-b form alters NFκB activity, we performed transient transfection assays to analyze the effects of Mdm2-b on NFκB-mediated gene expression. For these experiments we elected to use 293T cells to examine Mdm2-b effects in non-fibroblast cells and because TNF-induction of NFκB activity has been well studied in this system. Furthermore, p53 is functionally inactivated in these cells (Grand et al., Virology 210:323-334 (1995)), thus any effects of the b isoform on NFκB activity should be independent of the Mdm2-p53 signaling pathway. Cotransfection of either Mdm2-b or Mdm2-bssp1 along with a luciferase gene placed under transcriptional control of a promoter containing canonical kB recognition sequences was performed in 293T cells. The presence of Mdm2-b resulted in increased expression of the NFκB-induced reporter gene, suggesting that the elevated levels of RelA induced by Mdm2-b leads to activation of the NFκB -responsive promoter. Furthermore, the presence of Mdm2-b increased the response of the NFκB promoter to TNF alpha stimulation in this experiment and in 3 repeat experiments. Although the mutated Mdm2-b$^{ssp1}$ was capable of enhancing TNF activation of the NFκB -responsive promoter (FIG. 3E), the level of TNF activation was clearly compromised by the presence of the RING mutation. Thus, the RING domain of Mdm2-b required for Mdm2-b mediated inhibition of apoptosis in our previous assays is also capable of altering NFκB activity in cells.

Example 5

Tumorigenesis in Mdm2-b Transgenic Mice

Mdm2-b transgenic mice were generated to assess the transforming capabilities of the Mdm2-b isoform in vivo. Initially, Mdm2-b was engineered into pCAGGS, which contains a CMV enhancer coupled to a chicken β-Actin promoter element, to promote Mdm2-b transgene expression in a ubiquitous manner in mice (FIG. 4a). Although multiple rounds of pronuclear injections using the CAGGS-Mdm2-b transgene were performed, no founder mice were generated. In contrast, a 15-20% founder rate is typically obtained using other transgene constructs in similar pronuclear injection experiments. This result suggests that widespread expression of Mdm2-b is incompatible with normal development, similar to what was previously observed using full-length Mdm2 cDNA as a transgene.

To avoid putative embryonic lethality, the glial fibrillary acidic protein (GFAP) promoter was fused to the Mdm2-b to generate transgenic mice that would display tissue-restricted expression of Mdm2-b (FIG. 4a). Seven lines of Gfap-Mdm2-b transgenic mice were identified by tail biopsy, three of which were eliminated from the study because they did not express the transgene in any tissue. Three remaining independent lines of Mdm2-b transgenic mice (B19, B31, and B45) were expanded for analysis and for tumor studies. Densitometry experiments performed on Southern blots of representative mice from each line indicated that lines B19 and B31 integrated 2 and 4 copies of the transgene, respectively, while line B45 had integrated 25 copies of the transgene, however, spatial expression of the transgene was similar in all lines, and the levels of transgene expression was likewise similar across all lines. Northern analysis of RNA isolated from a variety of tissues indicated that all lines of mice displayed the highest levels of Gfap-Mdm2-b expression in the brain and, to a lesser extent, the spleen. However, lower levels of transgene expression were readily detected in liver, kidney, ovary, and testes using RT-PCR against total RNA isolated from these tissues (FIG. 4b). Specificity of the resulting PCR products was confirmed by Southern analysis with an internal oligonucleotide. This pattern of transgene expression is very similar to the expression pattern seen in other transgenic mice generated using the GFAP promoter to drive transgene expression (Brenner and Messing, Methods 10:351-364 (1996), Weissenberger et al., Oncogene 14:2005-13 (1997)).

Approximately 20% of the Gfap-Mdm2-b mice from transgenic line B19 and B31 displayed uncoordinated motor movements, erratic circling behaviors, head-tilting, and weak muscular strength; these behaviors are not completely penetrant, and not all transgenic offspring from these affected mice displayed this phenotype. A small subset (8%) of Gfap-Mdm2-b mice from these two lines died from hydroencephaly between 4 weeks and 24 weeks of age. Histologic analysis of brain tissue revealed that the hydroencephalic mice display highly dilated ventricles with intraventricular bleeding and macrophage infiltration. Other lines of transgenic mice expressing reporter genes from the GFAP promoter do not present similar phenotypes in brain, thus it is likely that robust Mdm2-b expression induced by the GFAP promoter in the brain is the underlying cause of these abnormalities.

Figure 5A:
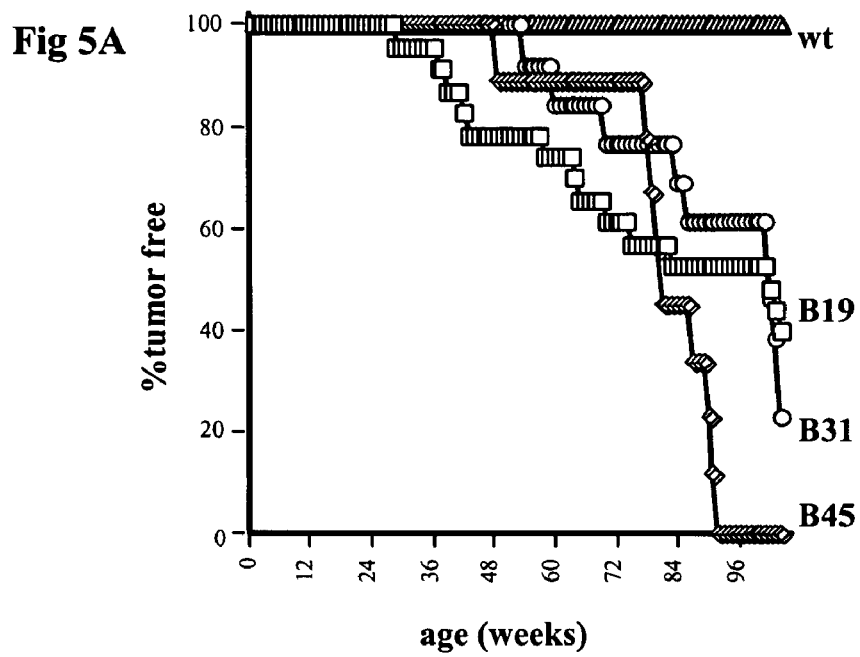
FIG. 5A is a Kaplan-Meir plot for 3 lines of GFAP-Mdm2-b transgenic mice showing that the average onset of tumorigenesis occurs at 44 weeks. Mice typically present with large abdominal tumors as detailed in FIG. 5B.
Figure 5B:
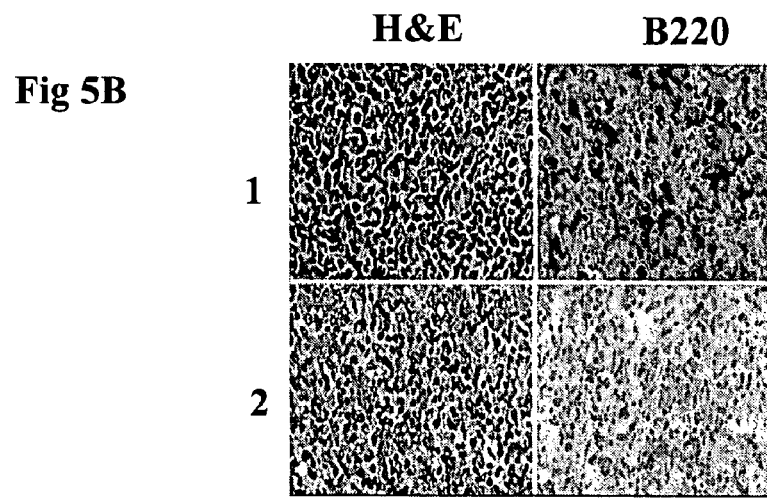
FIG. 5B is a set of four photomicrographs of hematoxylin and eosin stained (left column) or B220-antibody stained (right column) tumor sections. Antibody staining reveals a high percentage of B220-positive, B-cell lymphomas (row 1) and B220-negative, myeloid sarcomas (row 2). Analysis of myeloid sarcomas was confirmed by 2 independent pathologists and by positive staining for chloracetate esterase.

Cohorts of all 3 lines of Mdm2-b transgenic mice were monitored for spontaneous tumor development (FIG. 5a). Mice typically displayed large abdominal masses between 50 weeks and 104 weeks, with a mean time to tumorigenesis of 80 weeks for the B19 transgenic line, 84 weeks for the B31 transgenic line, and 100 weeks for the B45 transgenic line of mice. Portions of each tumor harvested from moribund mice at time of sacrifice were sent for histological examination as well as snap frozen for RNA and protein isolation. RNA isolated from several tumor samples confirmed Gfap-Mdm2-b transgene expression. Histologic analysis of tumors in the three lines of mice revealed that 70% of the tumors were myeloid sarcomas, a tumor mass of immature myeloid cells that occurred in an extramedullary site (see Table 1 below, for a representative listing of tumors). These tumors stained negative for B220 surface antigens and positive for chloroacetate esterase. Histopathology and B220 antibody staining confirmed that the remaining 30% of the tumors were B-cell lymphomas (FIG. 5b).

Figure 5C:
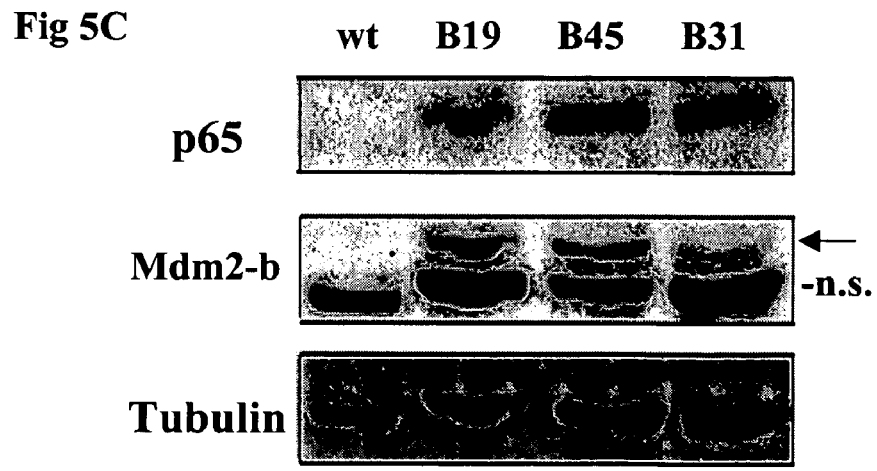
FIG. 5C is a representation of a Western blot of tumor samples obtained in three GFAP-Mdm2-b transgenic lines confirms the presence of Mdm2-b band (arrow) just above the non-specific band also observed in wt tissue. Elevated NFκB protein p65 was also observed in tumor samples. An antibody against tubulin was used as a control in this experiment.

To confirm the presence of the Mdm2-b in the tumors, a carboxy-terminal Mdm2 antibody (C-18) was used for detecting Mdm2-b protein. Three representative tumors obtained from Mdm2-b transgenic mice (one from each line) were analyzed for the presence of the Mdm2-b protein. A 47 Kd band corresponding to the Mdm2-b form was detected in all three samples and was absent in wildtype, non-transgenic mouse tissue (FIG. 5c). In addition, the RelA protein was specifically elevated in the Mdm2-b tumor tissues, similar to what was observed in the NIH3T3, Mdm2-b-transfected cells. Thus, the Mdm2-b isoform can induce spontaneous tumor formation in vivo.

TABLE 1

Representative tumors in Mdm2-b transgenic lines B19, B45, and B31

| Mouse | Age (weeks) | Tumor site | Pathology |
|---|---|---|---|
| 19-19 | 58 | throat (lymph), spleen | B cell lymphoma |
| 19-98 | 83 | spleen, lymph, lung | myeloid sarcoma |
| 19-103 | 104 | lymph | B cell lymphoma |
| 19-100 | 102 | spleen, liver | myeloid sarcoma |
| 19-105 | 104 | lymph | myeloid sarcoma |
| 19-126 | 70 | abdominal mass, spleen | myeloid sarcoma |
| 45-93 | 80 | lymph | B cell lymphoma |
| 45-45 | 91 | spleen, lymph, liver, lungs | myeloid sarcoma |
| 45-94 | 87 | abdominal mass, kidney, lung | myeloid sarcoma |
| 45-92 | 92 | spleen, lymph, liver, lungs | myeloid sarcoma |
| 31-31 | 104 | spleen, lymph | myeloid sarcoma |
| 31-68 | 104 | abdominal mass, spleen, liver | myeloid sarcoma |
| 31-122 | 84 | abdominal mass, spleen, liver | myeloid sarcoma |
| 31-161 | 70 | chest mass, spleen | B cell lymphoma |
| 31-33 | 104 | lymph | myeloid sarcoma |
| 31-70 | 102 | spleen, lymph, bowel | B cell lymphoma |
| 31-71 | 60 | spleen, lymph, lung | myeloid sarcoma |
| 31-163 | 86 | abdominal mass, spleen liver | myeloid sarcoma |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule comprising a sequence encoding an Mdm2-b polypeptide comprising an amino acid sequence that is at least 95% identical to the full length of SEQ ID NO:12, wherein the polypeptide can inhibit apoptosis in a cell, or the full-length complement thereof.

2. An isolated nucleic acid molecule comprising SEQ ID NO:11, or the full-length complement thereof.

3. The isolated nucleic acid molecule of claim 1, wherein the nucleic acid encodes a polypeptide comprising SEQ ID NO:12.

4. An expression vector comprising the isolated nucleic acid sequence of claim 1.

5. An isolated host cell comprising the expression vector of claim 4.

6. An isolated nucleic acid molecule consisting of SEQ ID NO:11, or the full-length complement thereof.

7. An isolated nucleic acid molecule that is at least 95% identical to the full length of SEQ ID NO:11, and encodes an Mdm2-b polypeptide comprising an amino acid sequence that is at least 95% identical to the full length of SEQ ID NO:12, wherein the polypeptide can inhibit apoptosis in a cell, or the full-length complement thereof.

* * * * *